United States Patent
Christensen, IV et al.

(10) Patent No.: US 6,300,372 B1
(45) Date of Patent: *Oct. 9, 2001

(54) 3-CYANO-3-(3,4-DISUBSTITUTED) PHENYLCYCLOHEXYL-1-CARBOXYLATES

(75) Inventors: Siegfried B. Christensen, IV, Philadelphia; Cornelia Jutta Forster, Bensalem, both of PA (US)

(73) Assignee: SmithKline Beecham Corporation, Philadelphia, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/586,770
(22) PCT Filed: Jul. 29, 1994
(86) PCT No.: PCT/US94/08581
  § 371 Date: Jan. 30, 1996
  § 102(e) Date: Jan. 30, 1996
(87) PCT Pub. No.: WO95/03794
  PCT Pub. Date: Feb. 9, 1995
(51) Int. Cl.$^7$ .................. C07C 255/45; A61K 31/275
(52) U.S. Cl. ............................ 514/521; 558/407
(58) Field of Search .................. 558/407; 514/521

(56) References Cited

U.S. PATENT DOCUMENTS

| 2,573,015 | 10/1951 | Hafliger et al. |
| 2,650,243 | 8/1953 | Novello . |
| 2,822,383 | 2/1958 | Smith . |
| 2,886,589 | 5/1959 | Novello . |
| 2,911,432 | 11/1959 | Hoehm . |
| 5,552,438 | 9/1996 | Christensen . |

FOREIGN PATENT DOCUMENTS

95/09836 * 4/1995 (WO) .................. 514/520

OTHER PUBLICATIONS

Kalre, Indian J. Chem. 1972 10(5) 467–9, Abstract Only.*

* cited by examiner

Primary Examiner—Robert Gerstl
(74) Attorney, Agent, or Firm—James M. Kanagy; Charles M. Kinzig

(57) ABSTRACT

Novel 3-cyano-3-(3,4-disubstituted)phenylcyclohexyl-1-carboxylates or derivatives thereof and their corresponding cyclohexenyl analogs are described herein. These compounds inhibit the production of Tumor Necrosis Factor and are useful in the treatment of disease states mediated or exacerbated by TNF production. These compounds are also useful mediating or inhibiting the enzymatic or catalytic activity of phosphodiesterase IV and are therefore useful in treating diseases in need of mediation or inhibition thereof.

4 Claims, No Drawings

3-CYANO-3-(3,4-DISUBSTITUTED) PHENYLCYCLOHEXYL-1-CARBOXYLATES

FIELD OF INVENTION

The present invention relates to certain novel 3-cyano-3-(3,4-disubstituted)phenylcyclohexyl-1-carboxylates and their corresponding cyclohexenyl analogs, pharmaceutical compositions containing these compounds, and their use in treating allergic and inflammatory diseases and for inhibiting the production of Tumor Necrosis Factor (TNF).

BACKGROUND OF THE INVENTION

Bronchial asthma is a complex, multifactorial disease characterized by reversible narrowing of the airway and hyperreactivity of the respiratory tract to external stimuli.

Identification of novel therapeutic agents for asthma is made difficult by the fact that multiple mediators are responsible for the development of the disease. Thus, it seems unlikely that eliminating the effects of a single mediator will have a substantial effect on all three components of chronic asthma. An alternative to the "mediator approach" is to regulate the activity of the cells responsible for the pathophysiology of the disease.

One such way is by elevating levels of cAMP (adenosine cyclic 3',5'-monophosphate). Cyclic AMP has been shown to be a second messenger mediating the biologic responses to a wide range of hormones, neurotransmitters and drugs; [Krebs Endocrinology Proceedings of the 4th International Congress Excerpta Medica, 17–29, 1973]. When the appropriate agonist binds to specific cell surface receptors, adenylate cyclase is activated, which converts $Mg^{+2}$-ATP to cAMP at an accelerated rate.

Cyclic AMP modulates the activity of most, if not all, of the cells that contribute to the pathophysiology of extrinsic (allergic) asthma. As such, an elevation of cAMP would produce beneficial effects including: 1) airway smooth muscle relaxation, 2) inhibition of mast cell mediator release, 3) suppression of neutrophil degranulation, 4) inhibition of basophil degranulation, and 5) inhibition of monocyte and macrophage activation. Hence, compounds that activate adenylate cyclase or inhibit phosphodiesterase should be effective in suppressing the inappropriate activation of airway smooth muscle and a wide variety of inflammatory cells. The principal cellular mechanism for the inactivation of cAMP is hydrolysis of the 3'-phosphodiester bond by one or more of a family of isozymes referred to as cyclic nucleotide phosphodiesterases (PDEs).

It has now been shown that a distinct cyclic nucleotide phosphodiesterase (PDE) isozyme, PDE IV, is responsible for cAMP breakdown in airway smooth muscle and inflammatory cells. [Torphy, "Phosphodiesterase Isozymes: Potential Targets for Novel Anti-asthmatic Agents" in New Drugs for Asthma, Barnes, ed. IBC Technical Services Ltd., 1989]. Research indicates that inhibition of this enzyme not only produces airway smooth muscle relaxation, but also suppresses degranulation of mast cells, basophils and neutrophils along with inhibiting the activation of monocytes and neutrophils. Moreover, the beneficial effects of PDE IV inhibitors are markedly potentiated when adenylate cyclase activity of target cells is elevated by appropriate hormones or autocoids, as would be the case in vivo. Thus PDE IV inhibitors would be effective in the asthmatic lung, where levels of prostaglandin $E_2$ and prostacyclin (activators of adenylate cyclase) are elevated. Such compounds would offer a unique approach toward the pharmacotherapy of bronchial asthma and possess significant therapeutic advantages over agents currently on the market.

The compounds of this invention also inhibit the production of Tumor Necrosis Factor (TNF), a serum glycoprotein. Excessive or unregulated TNF production has been implicated in mediating or exacerbating a number of diseases including rheumatoid arthritis, rheumatoid spondylitis, osteoarthritis, gouty arthritis and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, reperfusion injury, graft vs. host reaction, allograft rejections, fever and myalgias due to infection, such as influenza, cachexia secondary to infection or malignancy, cachexia secondary to human acquired immune deficiency syndrome (AIDS), AIDS, ARC (AIDS related complex), keloid formation, scar tissue formation, Crohn's disease, ulcerative colitis, or pyresis, in addition to a number of autoimmune diseases, such as multiple sclerosis, autoimmune diabetes and systemic lupus erythematosis.

AIDS results from the infection of T lymphocytes with Human Immunodeficiency Virus (HIV). At least three types or strains of HIV have been identified, i.e., HIV-1, HIV-2 and HIV-3. As a consequence of HIV infection, T-cell-mediated immunity is impaired and infected individuals manifest severe opportunistic infections and/or unusual neoplasms. HIV entry into the T lymphocyte requires T lymphocyte activation. Viruses such as HIV-1 or HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication.

Cytokines, specifically TNF, are implicated in activated T-cell-mediated HIV protein expression and/or virus replication by playing a role in maintaining T lymphocyte activation. Therefore, interference with cytokine activity such as by inhibition of cytokine production, notably TNF, in an HIV-infected individual aids in limiting the maintenance of T cell activation, thereby reducing the progression of HIV infectivity to previously uninfected cells which results in a slowing or elimination of the progression of immune dysfunction caused by HIV infection. Monocytes, macrophages, and related cells, such as kupffer and glial cells, have also been implicated in maintenance of the HIV infection. These cells, like T cells, are targets for viral replication and the level of viral replication is dependent upon the activation state of the cells. [See Rosenberg et al., The Immunopathogenesis of HIV Infection, Advances in Immunology, Vol. 57, 1989]. Monokines, such as TNF, have been shown to activate HIV replication in monocytes and/or macrophages [See Poli et al., Proc. Natl. Acad. Sci., 87:782–784, 1990], therefore, inhibition of monokine production or activity aids in limiting HIV progression as stated above for T cells.

TNF has also been implicated in various roles with other viral infections, such as the cytomegalovirus (CMV), influenza virus, adenovirus, and the herpes virus for similar reasons as those noted.

TNF is also associated with yeast and fungal infections. Specifically *Candida albicans* has been shown to induce TNF production in vitro in human monocytes and natural killer cells [See Riipi et al., Infection and Immunity, 58(9): 2750–54, 1990; and Jafari et al., Journal of Infectious Diseases, 164:389–95, 1991. See also Wasan et al., Antimicrobial Agents and Chemotherapy, 35,(10):2046–48, 1991; and Luke et al., Journal of Infectious Diseases, 162:211–214,1990].

The ability to control the adverse effects of TNF is furthered by the use of the compounds which inhibit TNF in mammals who are in need of such use. There remains a need for compounds which are useful in treating TNF-mediated disease states which are exacerbated or caused by the excessive and/or unregulated production of TNF.

SUMMARY OF THE INVENTION

This invention relates to the novel compounds of Formula (I), as shown below, useful in the mediation or inhibition of the enzymatic activity (or catalytic activity) of phosphodiesterase IV (PDE IV). The novel compounds of Formula (I) also have Tumor Necrosis Factor (TNF) inhibitory activity.

This invention also relates to the pharmaceutical compositions comprising a compound of Formula (I) and a pharmaceutically acceptable carrier or diluent.

The invention also relates to a method of mediation or inhibition of the enzymatic activity (or catalytic activity) of PDE IV in mammals, including humans, which comprises administering to a mammal in need thereof an effective amount of a compound of Formula (I), as shown below.

The invention further provides a method for the treatment of allergic and inflammatory disease which comprises administering to a mammal, including humans, in need thereof, an effective amount of a compound of Formula (I).

The invention also provides a method for the treatment of asthma which comprises administering to a mammal, including humans, in need thereof, an effective amount of a compound of Formula (I).

This invention also relates to a method of inhibiting TNF production in a mammal, including humans, which method comprises administering to a mammal in need of such treatment, an effective TNF inhibiting amount of a compound of Formula (I). This method may be used for the prophylactic treatment or prevention of certain TNF mediated disease states amenable thereto.

This invention also relates to a method of treating a human afflicted with a human immunodeficiency virus (HIV), which comprises administering to such human an effective TNF inhibiting amount of a compound of Formula (I).

The compounds of Formula (I) are also useful in the treatment of additional viral infections, where such viruses are sensitive to upregulation by TNF or will elicit TNF production in vivo.

The compounds of Formula (I) are also useful in the treatment of yeast and fungal infections, where such yeast and fungi are sensitive to upregulation by TNF or will elicit TNF production in vivo.

The compounds of this invention are represented by Formula (I):

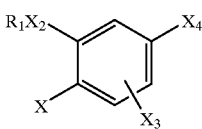

(I)

wherein:
$R_1$ is $-(CR_4R_5)_nC(O)O(CR_4R_5)_mR_6$, $-(CR_4R_5)_nC(O)NR_4(CR_4R_5)_mR_6$, $-(CR_4R_5)_nO(CR_4R_5)_mR_6$, or $-(CR_4R_5)_rR_6$ wherein the alkyl moieties may be optionally substituted with one or more halogens;
m is 0 to 2;
n is 1 to 4;
r is 0 to 6;
$R_4$ and $R_5$ are independently selected from hydrogen or a $C_{1-2}$ alkyl;
$R_6$ is hydrogen, methyl, hydroxyl aryl, halo substituted aryl, aryloxyC$_{1-3}$ alkyl, halo substituted aryloxyC$_{1-3}$ alkyl indanyl, indenyl, $C_{7-11}$ polycycloalkyl, tetahydrofuranyl, furanyl tetrahydropyranyl, pyranyl, tetrahydrothienyl, thienyl, tetrahydrothiopyranyl, thiopyranyl $C_{3-6}$ cycloalkyl, or a $C_{4-6}$ cycloalkyl containing one or two unsaturated bonds, wherein the cycloalkyl and heterocyclic moieties may be optionally substituted by 1 to 3 methyl groups or one ethyl group;
provided that:
a) when $R_6$ is hydroxyl, then m is 2; or
b) when $R_6$ is hydroxyl, then r is 2 to 6; or
c) when $R_6$ is 2-tetrahydropyranyl, 2-tetrahydrothiopyranyl, 2-tetrahydrofuranyl, or 2-tetrahydrothienyl, then m is 1 or 2; or
d) when $R_6$ is 2-tetrahydropyranyl, 2-tetrahydrothiopyranyl, 2-tetrahydrofuranyl, or 2-tetrahydrothienyl, then r is 1 to 6;
e) when n is 1 and m is 0, then $R_6$ is other than H in $-(CR_4R_5)_nO(CR_4R_5)_mR_6$;
X is $YR_2$, halogen, nitro, $NR_4R_5$, or formyl amine;
Y is O or $S(O)_{m'}$;
m' is 0, 1, or 2;
$X_2$ is O or $NR_8$;
$X_3$ is hydrogen or X;
$X_4$ is

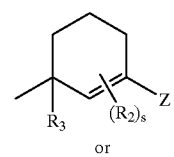

(a)

or

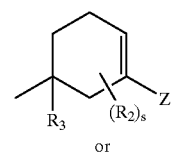

(b)

or

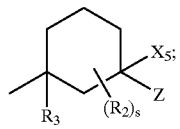

(c)

$X_5$ is H, $R_9$, $OR_8$, CN, $C(O)R_8$, $C(O)OR_8$, $C(O)NR_8R_8$, or $NR_8R_8$;
$R_2$ is independently $-CH_3$ or $-CH_2CH_3$ optionally substituted by 1 or more halogens;
s is 0 to 4;
$R_3$ is hydrogen, halogen, $C_{1-4}$ alkyl, $CH_2NHC(O)C(O)NH_2$, halo-substituted $C_{1-4}$ alkyl, $-CH=CR_8'R_8'$, cyclopropyl optionally substituted by $R_8'$, CN, $OR_8$, $CH_2OR_8$, $NR_8R_{10}$, $CH_2NR_8R_{10}$, $C(Z')H$, $C(O)OR_8$, $C(O)NR_8R_{10}$, or $C\equiv CR_8'$;
Z' is O, $NR_9$, $NOR_8$, NCN, $C(-CN)_2$, $CR_8CN$, $CR_8NO_2$, $CR_8C(O)OR_8$, $CR_8C(O)NR_8R_8$, $C(-CN)NO_2$, $C(-CN)C(O)OR_9$, or $C(-CN)C(O)NR_8R_8$;

Z is $C(Y')R_{14}$, $C(O)OR_{14}$, $C(Y')NR_{10}R_{14}$, $C(NR_{10})NR_{10}R_{14}$, CN, $C(NOR_8)R_{14}$, $C(O)NR_8NR_8C(O)R_8$, $C(O)NR_8NR_{10}R_{14}$, $C(NOR_{14})R_8$, $C(NR_8)NR_{10}R_{14}$, $C(NR_{14})NR_8R_8$, $C(NCN)NR_{10}R_{14}$, $C(NCN)SR_9$, (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl); wherein all of the heterocyclic ring systems may be optionally substituted one or more times by $R_{14}$;

Y' is O or S;

$R_7$ is —$(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, —F, —Br, —Cl, —$NO_2$, —$NR_{10}R_{11}$, —$C(O)R_8$, —$C(O)OR_8$, —$OR_8$, —CN, —$C(O)NR_{10}R_{11}$, —$OC(O)NR_{10}R_{11}$, —$OC(O)R_8$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —$C(NCN)NR_{10}R_{11}$, —$C(NCN)SR_9$, —$NR_{10}C(NCN)SR_9$, —$NR_{10}C(NCN)NR_{10}R_{11}$, —$NR_{10}S(O)_2R_9$, —$S(O)_{m'}R_9$, —$NR_{10}C(O)C(O)NR_{10}R_{11}$, —$NR_{10}C(O)C(O)R_{10}$, thiazolyl, imidazolyl, oxazolyl, pyrazolyl, triazolyl or tetrazolyl;

q is 0, 1, or 2;

$R_{12}$ is $C_{3-7}$ cycloalkyl, (2-, 3- or 4-pyridyl), pyrimidyl, pyrazolyl, (1- or 2-imidazolyl), thiazolyl, triazolyl, pyrrolyl, piperazinyl, piperidinyl, morpholinyl, furanyl, (2- or 3-thienyl), (4- or 5-thiazolyl), quinolinyl, naphthyl, or phenyl;

$R_8$ is hydrogen or $R_9$;

$R_{8'}$ is $R_8$ or fluorine;

$R_9$ is $C_{1-4}$ alkyl optionally substituted by one to three fluorines;

$R_{10}$ is $OR_8$ or $R_{11}$;

$R_{11}$ is hydrogen, or $C_{1-4}$ alkyl optionally substituted by one to three fluorines; or when $R_{10}$ and $R_{11}$ are as $NR_{10}R_{11}$ they may together with the nitrogen form a 5 to 7 membered ring optionally containing at least one additional heteroatom which is O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_{10}$ and $R_{14}$ are as $NR_{10}R_{14}$ they may together with the nitrogen form a 5 to 7 membered ring optionally containing at least one additional heteroatom which is O, N, or S;

provided that:

f) when $R_{12}$ is N-pyrazolyl, N-imidazolyl, N-triazolyl, N-pyrrolyl, N-piperazinyl, N-piperidinyl, or N-morpholinyl, then q is not 1; or or the pharmaceutically acceptable salts thereof.

DETAILED DESCRIPTION OF THE INVENTION

This invention relates to the novel compounds of Formula (I), and to pharmaceutical compositions comprising a compound of Formula (I) and a pharmaceutically acceptable carrier or diluent. This invention also relates to a method of mediating or inhibiting the enzymatic (or catalytic activity) of PDE IV in a mammal in need thereof and to inhibiting the production of TNF in a mammal in need thereof, which comprises administering to said mammal an effective amount of a compound of Formula (I).

Phosphodiesterase IV inhibitors are useful in the treatment of a variety of allergic and inflammatory diseases including: asthma, chronic bronchitis, atopic dermatitis, urticaria, allergic rhinitis, allergic conjunctivitis, vernal conjunctivitis, eosinophilic granuloma, psoriasis, rheumatoid arthritis, septic shock, ulcerative colitis, Crohn's disease, reperfusion injury of the myocardium and brain, chronic glomerulonephritis, endotoxic shock and adult respiratory distress syndrome. In addition, PDE IV inhibitors are useful in the treatment of diabetes insipidus, [Kidney Int., 37:362, 1990; Kidney Int., 35:494, 1989] and central nervous system disorders such as depression and multi-infarct dementia.

The compounds of Formula (I) are also useful in the treatment of viral infections, where such viruses are sensitive to upregulation by TNF or will elicit TNF production in vivo. The viruses contemplated for treatment herein are those that produce TNF as a result of infection, or those which are sensitive to inhibition, such as by deceased replication, directly or indirectly, by the TNF inhibitors of Formula (1). Such viruses include, but are not limited to HIV-1, HIV-2 and HIV-3, cytomegalovirus (CMV), influenza, adenovirus and the Herpes group of viruses, such as, but not limited to, *Herpes zoster* and *Herpes simplex*.

This invention more specifically relates to a method of treating a mammal, afflicted with a human immunodeficiency virus (HIV), which comprises administering to such mammal an effective TNF inhibiting amount of a compound of Formula (I).

The compounds of Formula (I) may also be used in association with the veterinary treatment of animals, other than in humans, in need of inhibition of TNF production. TNF mediated diseases for treatment, therapeutically or prophylactically, in animals include disease states such as those noted above, but in particular viral infections. Examples of such viruses include, but are not limited to feline immunodeficiency virus (FIV) or other retroviral infection such as equine infectious anemia virus, caprine arthritis virus, visna virus, maedi virus and other lentiviruses.

The compounds of Formula (I) are also useful in the treatment of yeast and fungal infections, where such yeast and fungi are sensitive to upregulation by TNF or will elicit TNF production in vivo. A preferred disease state for treatment is fungal meningitis. Additionally, the compounds of Formula (I) may be administered in conjunction with other drugs of choice for systemic yeast and fungal infections. Drugs of choice for fungal infections, include but are not limited to the class of compounds called the polymixins, such as Polymycin B, the class of compounds called the imidazoles, such as clotrimazole, econazole, miconazole, and ketoconazole; the class of compounds called the triazoles, such as fluconazole, and itranazole, and the class of compound called the Amphotericins, in particular Amphotericin B and liposomal Amphotericin B.

The co-administration of the anti-fungal agent with a compound of Formula (I) may be in any preferred composition for that compound such as is well known to those skilled in the art, for instance the various Amphotericin B formulations. Co-administration of an anti-fungal agent with a compound of Formula (I) may mean simultaneous administration or in practice, separate administration of the agents to the mammal but in a consecutive manner. In particular, the compounds of Formula (I) may be co-administered with a formulation of Amphotericin B, notably for systemic fungal infections. The preferred organism for treatment is the Candida organism. The compounds of Formula (I) may be co-administered in a similar manner with anti-viral or anti-bacterial agents.

The compounds of Formula (I) may also be used for inhibiting and/or reducing the toxicity of an anti-fungal, anti-bacterial or anti-viral agent by administering an effective amount of a compound of Formula (I) to a mammal in need of such treatment. Preferably, a compound of Formula (I) is administered for inhibiting or reducing the toxicity of the Amphotericin class of compounds, in particular Amphotericin B.

When $R_1$ for the compounds of Formula (I) is an alkyl substituted by 1 or more halogens, the halogens are preferably fluorine and chlorine, more preferably a $C_{1-4}$ alkyl substituted by 1 or more fluorines. The preferred halo-substituted alkyl chain length is one or two carbons, and most preferred are the moieties —$CF_3$, —$CH_2F$, —$CHF_2$, —$CF_2CHF_2$, —$CH_2CF_3$, and —$CH_2CHF_2$. Preferred $R_1$ substitutents for the compounds of Formula (I) are $CH_2$-cyclopropyl, $CH_2$—$C_{5-6}$ cycloalkyl, $C_{4-6}$ cycloalkyl $C_{7-11}$ polycycloalkyl, (3- or 4-cyclopentenyl), phenyl, tetrahydrofuran-3-yl, benzyl or $C_{1-2}$ alkyl optionally substituted by 1 or more fluorines, —$(CH_2)_{1-3}C(O)O(CH_2)_{0-2}CH_3$, —$(CH_2)_{1-3}O(CH_2)_{0-2}CH_3$, and —$(CH_2)_{2-4}OH$.

When the $R_1$ term contains the moiety $(CR_4R_5)$, the $R_4$ and $R_5$ terms are independently hydrogen or alkyl. This allows for branching of the individual methylene units as $(CR_4R_5)_n$ or $(CR_4R_5)_m$; each repeating methylene unit is independent of the other, e.g., $(CR_4R_5)_n$ wherein n is 2 can be –$CH_2CH(—CH_3)$—, for instance. The individual hydrogen atoms of the repeating methylene unit or the branching hydrocarbon can optionally be substituted by fluorine independent of each other to yield, for instance, the preferred $R_1$ substitutions, as noted above.

When $R_1$ is a $C_{7-11}$ polycycloalkyl, examples are bicyclo[2.2.1]-heptyl, bicyclo[2.2.2]octyl, bicyclo[3.2.1]octyl, tricyclo[5.2.1.0$^{2,6}$]decyl, etc. additional examples of which are described in Saccamano et al., WO 87/06576, published Nov. 5, 1987, which disclosure is incorporated herein by reference in its entirety.

Z is preferably $C(O)R_8$, $C(O)OR_8$, $C(O)NR_8R_8$, $C(NR_8)NR_8R_8$, CN, $C(NOR_8)R_8$, $C(O)NR_8NR_8C(O)R_8$, C(NCN)$NR_8R_8$, $C(NCN)SR_9$, (1-, 4- or 5-{$R_8$}-2-imidazolyl), (1-, 4- or 5-{$R_8$}-3-pyrazolyl), (1-, 2- or 5-{$R_8$}-4-triazolyl[1,2,3]), (1-, 2-, 4- or 5-{$R_8$}-3-triazolyl[1,2,4]), (1- or 2-{$R_8$}-5-tetrazolyl), (4- or 5-{$R_8$}-2-oxazolyl), (3- or 4-{$R_8$}-5-isoxazolyl), (3-{$R_8$}-5-oxadiazolyl[1,2,4]), (5-{$R_8$}-3-oxadiazolyl[1,2,4]), (5-{$R_8$}-2-oxadiazolyl[1,3,4]), (5-{$R_8$}-2-thiadiazolyl[1,3,4]), (4- or 5-{$R_8$}-2-thiazolyl), (4- or 5-{$R_8$}-2-oxazolidinyl), (4- or 5-{$R_8$}-2-thiazolidinyl),(1-, 4- or 5-{$R_8$}-2-imidazolidinyl); most preferred are those compounds wherein the $R_8$ group of Z is $R_4$.

$X_5$ is preferably hydrogen, $C_{1-2}$ alkyl optionally substituted by one to three fluorines, $OR_8$, CN, $C(O)R_8$, $C(O)OR_8$, $C(O)NR_8R_8$, or $NR_8R_8$.

Preferred X groups for Formula (I) are those wherein X is $YR_2$ and Y is oxygen. The preferred $X_2$ group for Formula (I) is that wherein $X_2$ is oxygen. The preferred $X_3$ group for Formula (I) is that wherein $X_3$ is hydrogen. Preferred $R_2$ groups, where applicable, are $C_{1-2}$ alkyl optionally substituted by 1 or more halogens. The halogen atoms are preferably fluorine and chlorine, more preferably fluorine. More preferred $R_2$ groups are those wherein $R_2$ is methyl, or the fluoro-substituted alkyls, specifically a $C_{1-2}$ alkyl, such as a —$CF_3$, —$CHF_2$, or —$CH_2CHF_2$ moiety. Most preferred are the —$CHF_2$ and —$CH_3$ moieties.

Preferred $R_3$ moieties are $C(O)NH_2$, $C \equiv CR_8$, CN, C(Z')H, $CH_2OH$, $CH_2F$, $CF_2H$, and $CF_3$. More preferred are $C \equiv CH$ and CN. Z' is preferably O or $NOR_8$.

Preferred $R_7$ moieties include optionally substituted —$(CH_2)_{1-2}$(cyclopropyl), —$(CH_2)_{0-2}$(cyclobutyl), —$(CH_2)_{0-2}$(cyclopentyl), —$(CH_2)_{0-2}$(cyclohexyl), —$(CH_2)_{0-2}$(2-, 3- or 4-pyridyl), —$(CH_2)_{1-2}$(2-imidazolyl), —$(CH_2)_2$(4-morpholinyl), —$(CH_2)_2$(4-piperazinyl), —$(CH_2)_{1-2}$(2-thienyl), —$(CH_2)_{1-2}$(4-thiazolyl), and —$(CH_2)_{0-2}$phenyl;

Preferred rings when $R_{10}$ and $R_{11}$ in the moiety —$NR_{10}R_{11}$ together with the nitrogen to which they are attached form a 5 to 7 membered ring optionally containing at least one additional heteroatom which is O, N, or S include, but are not limited to 1-imidazolyl, 2-($R_8$)-1-imidazolyl, 1-pyrazolyl, 3-($R_8$)-1-pyrazolyl, 1-triazolyl, 2-triazolyl, 5-($R_8$)-1-triazolyl, 5-($R_8$)-2-triazolyl, 5-($R_8$)-1-tetrazolyl, 5-($R_8$)-2-tetrazolyl, 1-tetrazolyl, 2-tetrazolyl, morpholinyl, piperazinyl, 4-($R_8$)-1-piperazinyl, or pyrrolyl ring.

Preferred rings when $R_{10}$ and $R_{14}$ in the moiety —$NR_{10}R_{14}$ together with the nitrogen to which they are attached may form a 5 to 7 membered ring optionally containing at least one additional heteroatom which is O, N, or S include, but are not limited to 1-imidazolyl, 1-pyrazolyl, 1-triazolyl, 2-triazolyl, 1-tetrazolyl, 2-tetrazolyl, morpholinyl, piperazinyl, and pyrrolyl. The respective rings may be additionally substituted, where applicable, on an available nitrogen or carbon by the moiety $R_7$ as described herein for Formula (I). Illustrations of such carbon substitutions includes, but are not limited to, 2-($R_7$)-1-imidazolyl, 4-($R_7$)-1-imidazolyl, 5-($R_7$)-1-imidazolyl, 3-($R_7$)-1-pyrazolyl, 4-($R_7$)-1-pyrazolyl, 5-($R_7$)-1-pyrazolyl, 4-($R_7$)-2-triazolyl, 5-($R_7$)-2-triazolyl, 4-($R_7$)-1-triazolyl, 5-($R_7$)-1-triazolyl, 5-($R_7$)-1-tetrazolyl, and 5-($R_7$)-2-triazolyl. Applicable nitrogen substitution by $R_7$ includes, but is not limited to, 1-($R_7$)-2-tetrazolyl, 2-($R_7$)-1-tetrazolyl, 4-($R_7$)-1-piperazinyl. Where applicable, the ring may be substituted one or more times by $R_7$.

Preferred groups for $NR_{10}R_{14}$ which contain a heterocyclic ring are 5-($R_{14}$)-1-tetrazolyl, 2-($R_{14}$)-1-imidazolyl, 5-($R_{14}$)-2-tetrazolyl, or 4-($R_{14}$)-1-piperazinyl.

Preferred rings for $R_{13}$ include (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4-, or 5-thiazolyl), (2-, 4-, or 5-oxazolidinyl), (2-, 4-, or 5-thiazolidinyl), or (2-, 4-, or 5-imidazolidinyl).

When the $R_7$ group is optionally substituted by a heterocyclic ring such as imidazolyl, pyrazolyl, triazolyl, tetrazolyl, or thiazolyl, the heterocyclic ring itself may be optionally substituted by $R_8$ either on an available nitrogen or carbon atom, such as 1-($R_8$)-2-imidazolyl, 1-($R_8$)-4-imidazolyl, 1-($R_8$)-5-imidazolyl, 1-($R_8$)-3-pyrazolyl, 1-($R_8$)-4-pyrazolyl, 1-($R_8$)-5-pyrazolyl, 1-($R_8$)-4-triazoyl, or 1-($R_8$)-5-triazolyl. Where applicable, the ring may be substituted one or more times by $R_8$.

Preferred are those compounds of Formula (I) wherein $R_1$ is —$CH_2$-cyclopropyl, —$CH_2$—$C_{5-6}$ cycloalkyl, —$C_{4-6}$ cycloalkyl, tetrahydrofuran-3-yl, (3- or 4-cyclopentenyl), benzyl or —$C_{1-2}$ alkyl optionally substituted by 1 or more fluorines, and —$(CH_2)_{2-4}$ OH; $R_2$ is methyl or fluoro-substituted alkyl, $R_3$ is CN or C≡$CR_8$; and X is $YR_2$.

Most preferred are those compounds wherein $R_1$ is —$CH_2$-cyclopropyl, cyclopentyl, methyl or $CF_2H$; $R_3$ is CN or C≡CH; X is $YR_2$; Y is oxygen; $X_2$ is oxygen; $X_3$ is hydrogen; and $R_2$ is $CF_2H$ or methyl. In most cases the cis configuration is preferred over the trans configuration. However, substituent pattern may influence the overall activity of these compounds in some manner which results in the trans configuration being the more active configuration. While the cis configuration is thought to be more active in most instances, this must be confirmed on for each compound.

A preferred subgenus of the compounds of Formula (I) is the group of compounds of Formula (Ia)

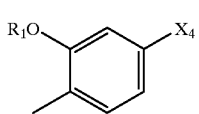

(Ia)

wherein:

$R_1$ is $CH_2$-cyclopropyl, $CH_2$—$C_{5-6}$ cycloalkyl, $C_{4-6}$ cycloalkyl, $C_{7-11}$ polycycloalkyl, (3- or 4-cyclopentenyl), phenyl, tetrahydrofuran-3-yl, benzyl or $C_{1-2}$ alkyl optionally substituted by 1 or more fluorines, —$(CH_2)_{1-3}C(O)O(CH_2)_{0-2}CH_3$, —$(CH_2)_{1-3}O(CH_2)_{0-2}CH_3$, and —$(CH_2)_{2-4})OH$;

X is $YR_2$, halogen, nitro, $NR_4R_5$, or formyl amine;

$X_4$ is

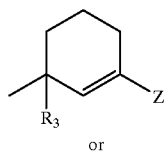

(a)

or

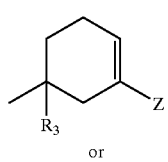

(b)

or

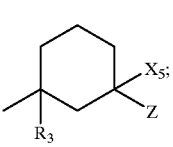

(c)

$X_5$ is H, $R_9$, $OR_8$, CN, C(O)$R_8$, C(O)$OR_8$, C(O)$NR_8R_8$, or $NR_8R_8$;

Y is O or S(O)$_{m'}$;

m' is 0, 1, or 2;

$R_2$ is —$CH_3$ or —$CH_2CH_3$ optionally substituted by 1 or more halogens;

$R_3$ is hydrogen, $C_{1-4}$ alkyl, $CH_2NHC(O)C(O)NH_2$, halo-substituted $C_{1-4}$ alkyl, CN, $CH_2OR_8$, C(Z')H, C(O)$OR_8$, C(O)$NR_8R_{10}$, or C≡$CR_8$;

Z' is O or $NOR_8$;

Z is C(O)$R_{14}$, C(O)$OR_{14}$, C(O)$NR_{10}R_{14}$, C($NR_{10}$)$NR_{10}R_{14}$, CN, C($NOR_8$)$R_{14}$, C(O)$NR_8NR_8C(O)R_8$, C(O)$NR_8NR_{10}R_{14}$, C($NOR_{14}$)$R_8$, C($NR_8$)$NR_{10}R_{14}$, C($NR_{14}$)$NR_8R_8$, C(NCN)$NR_{10}R_{14}$, C(NCN)$SR_9$, (1-, 4- or 5-{$R_{14}$}-2-imidazolyl), (1-, 4- or 5-{$R_{14}$}-3-pyrazolyl), (1-, 2- or 5-{$R_{14}$}-4-triazolyl[1,2,3]), (1-, 2-, 4- or 5-{$R_{14}$}-3-triazolyl[1,2,4]), (1- or 2-{$R_{14}$}-5-tetrazolyl), (4- or 5-{$R_{14}$}-2-oxazolyl), (3- or 4-{$R_{14}$}-5-isoxazolyl), (3-{$R_{14}$}-5-oxadiazolyl[1,2,4]), (5-{$R_{14}$}-3-oxadiazolyl[1,2,4]), (5-{$R_{14}$}-2-oxadiazolyl[1,3,4]), (5-{$R_{14}$}-2-thiadiazolyl[1,3,4]), (4- or 5-{$R_{14}$}-2-thiazolyl), (4- or 5-{$R_{14}$}-2-oxazolidinyl), (4- or 5-{$R_{14}$}-2-thiazolidinyl), (1-, 4- or 5-{$R_{14}$}-2-imidazolidinyl);

$R_7$ is —$(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, —F, —Br, —Cl, —$NO_2$, —$NR_{10}R_{11}$, —C(O)$R_8$, —C(O)$OR_8$, —$OR_8$, —CN, —C(O)$NR_{10}R_{11}$, —OC(O)$NR_{10}R_{11}$, —OC(O)$R_8$, —$NR_{10}$C(O)$NR_{10}R_{11}$, —$NR_{10}$C(O)$R_{11}$, —$NR_{10}$C(O)$OR_9$, —$NR_{10}$C(O)$R_{13}$, —C($NR_{10}$)$NR_{10}R_{11}$, —C(NCN)$NR_{10}R_{11}$, —C(NCN)$SR_9$, —$NR_{10}$C(NCN)$SR_9$, —$NR_{10}$C(NCN)$NR_{10}R_{11}$, —$NR_{10}S(O)_2R_9$, —S(O)$_{m'}R_9$, —$NR_{10}$C(O)C(O)$NR_{10}R_{11}$, —$NR_{10}$C(O)C(O)$R_{10}$, thiazolyl, imidazolyl, oxazolyl, pyrazolyl, triazolyl, or tetrazolyl;

q is 0, 1, or 2;

$R_{12}$ is $C_3$–$C_7$ cycloalkyl, (2-, 3- or 4-pyridyl), (1- or 2-imidazolyl), piperazinyl, morpholinyl, (2- or 3-thienyl), (4- or 5-thiazolyl), or phenyl;

$R_8$ is independently selected from hydrogen or $R_9$;

$R_9$ is $C_{1-4}$ alkyl optionally substituted by one to three fluorines;

$R_{10}$ is $OR_8$ or $R_{11}$;

$R_{11}$ is hydrogen or $C_{1-4}$ alkyl optionally substituted by one to three fluorines; or, when $R_{10}$ and $R_{11}$ are as $NR_{10}R_{11}$ they may together with the nitrogen form a 5 to 7 membered ring optionally containing at least one additional heteroatom which is O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_{10}$ and $R_{14}$ are as $NR_{10}R_{14}$ they may together with the nitrogen form a 5 to 7 membered ring optionally containing one or more additional heteroatoms which is O, N, or S;

provided that:
a) when $R_{12}$ is N-imidazolyl, N-triazolyl, N-pyrrolyl, N-piperazinyl, or N-morpholinyl, then q is not 1; or or the pharmaceutically acceptable salts thereof.

Exemplified compounds of Formula (I) are:

methyl 5-cyano-5-(3-cyclopropylmethoxy-4-methoxyphenyl)cyclohex-1-ene-1-carboxylate; SB 212179 ethyl 5-cyano-5-(3-cyclopropylmethoxy-4-methoxyphenyl)cyclohex-1-ene-1-carboxylate; SB methyl 5-cyano-5-(3-cyclopentyloxy-4-methoxyphenyl)cyclohex-1-ene-1-carboxylate; SB 211572 methyl 5-(3,4-bisdifluoromethoxyphenyl)-5-cyanocyclohex-1-ene-1-carboxylate; SB methyl cis-[3-cyano-3-(3-cyclopropylmethoxy-4-methoxyphenyl)-cyclohexane-1-carboxylate]; SB 210667 ethyl cis-[3-cyano-3-(3-cyclopropylmethoxy-4-methoxyphenyl)-cyclohexane-1-carboxylate]; SB 211600
methyl cis-[3-cyano-3-(3-cyclopentyloxy-4-methoxyphenyl)cyclohexane-1-carboxylate]; SB 212066
methyl cis-[3-(3,4-bisdifluoromethoxyphenyl)-3-cyanocyclohexane-1-carboxylate]; SB
cis-[3-cyano-3-(3-cyclopropylmethoxy-4-methoxyphenyl)cyclohexane-1-carboxylic acid]; SB 210984
cis-[3-cyano-3-(3-cyclopentyloxy-4-methoxyphenyl)cyclohexane-1-carboxylic acid]; SB 212510
cis-[3-cyano-3-(3-cyclopropylmethoxy-4-methoxyphenyl)cyclohexane-1-carboxamide]; SB 211529
cis-[3-cyano-3-(3-cyclopropylmethoxy-4-methoxyphenyl)cyclohexane-1-N-methylcarboxamide]; SB 213021
cis-[3-cyano-3-(3-cyclopropylmethoxy-4-methoxyphenyl)cyclohexane-1-N,N-dimethylcarboxamide]; SB 212697
cis-[3-cyano-3-(3-cyclopropylmethoxy-4-methoxyphenyl)cyclohexane-1-{N-(4-bromobenzyl)carboxamide}]; SB 212698
cis-[3-cyano-3-(3-cyclopentyloxy-4-methoxyphenyl)cyclohexane-1-carboxamide]; SB 214236
cis-[3-(3-cyclopropylmethoxy-4-methoxyphenyl)-1,3-dicyano-cyclohexane]; SB 212188
cis-[3-(3-cyclopentyloxy-4-methoxyphenyl)-1,3-dicyanocyclohexane]; SB 213832
cis-{3-cyano-3-(3-cyclopropylmethoxy-4-methoxyphenyl)-1-(3-methyl[1,2,4]oxadiazol-5-yl)cyclohexane}; SB 213826
cis-{3-cyano-3-(3-cyclopentyloxy-4-methoxyphenyl)-1-(3-methyl[1,2,4]-oxadiazol-5-yl)cyclohexane}; SB 214243
trans-[3-cyano-3-(3-cyclopropylmethoxy-4-methoxyphenyl)-cyclohexane-1-carboxylate]; SB 213677
trans-[3-cyano-3-(3-cyclopentyloxy-4-methoxyphenyl)-cyclohexane-1-carboxylate]; SB 213951
trans-[3-cyano-3-(3-cyclopropylmethoxy-4-methoxyphenyl)cyclohexane-1-carboxylic acid]; SB 213731
trans-[3-cyano-3-(3-cyclopentyloxy-4-methoxyphenyl)cyclohexane-1-carboxylic acid]; SB 213921
trans-[3-cyano-3-(3-cyclopropylmethoxy-4-methoxyphenyl)cyclohexane-1-carboxamide]; SB 213835
trans-[3-cyano-3-(3-cyclopentyloxy-4-methoxyphenyl)cyclohexane-1-carboxamide]; SB 213921
trans-[3-(3-cyclopropylmethoxy-4-methoxyphenyl)-1,3-dicyanocyclohexane]; SB 213920
trans-[3-(3-cyclopentyloxy-4-methoxyphenyl)-1,3-dicyanocyclohexane]; and SB 214241,
trans-{3-cyano-3-(3-cyclopentyloxyphenyl)-1-(3-methyl[1,2,4]oxadiazol-5-yl)cyclo-hexane}; SB 214242
methyl 3-cyano-3-(3-cyclopentyloxy-4-methoxyphenyl)cyclohex-1-ene-1-carboxylate;
methyl 5-cyano-5-(3-cyclopentyloxy-4-methoxyphenyl)cyclohex-1-ene-1-carboxylate;
3-(3-cyclopentyloxy-4-methoxyphenyl)cyclohex-1-ene-1,3-dicarbonitrile; and
5-(3-cyclopentyloxy-4-methoxyphenyl)cyclohex-1-ene-1,5-dicarbonitrile.

Some compounds of Formula (I) may exist in both racemic and optically active forms; some may also exist in distinct diastereomeric forms possessing distinct physical and biological properties. All of these compounds are considered to be within the scope of the present invention. Therefore another aspect of the present invention is the administration of either a racemate, a single enantiomeric form, a single diastereomeric form, or mixtures thereof.

The terms cis and trans denote stereochemistry at the C-1 position of the cyclohexane ring relative to the $R_3$ group at the C-3 position.

The terms "$C_{1-3}$ alkyl", "$C_{1-4}$ alkyl", "$C_{1-6}$ alkyl" or "alkyl" include both straight or branched chain radicals of 1 to 10, unless the chain length is limited thereto, including, but not limited to methyl, ethyl, n-propyl, isopropyl, n-butyl, sec-butyl, isobutyl, tert-butyl, and the like. "Alkenyl" includes both straight or branched chain radicals of 1 to 6 carbon lengths, unless the chain length is limited thereto, including but not limited to vinyl, 1-propenyl, 2-propenyl, 2-propynyl, or 3-methyl-2-propenyl. "Cycloalkyl" or "cycloalkyl alkyl" includes groups of 3–7 carbon atoms, such as cyclopropyl, cyclopropylmethyl, cyclopentyl, or cyclohexyl. "Aryl" or "aralkyl", unless specified otherwise, means an aromatic ring or ring system of 6 to 10 carbon atoms, such as phenyl, benzyl, phenethyl, or naphthyl. Preferably the aryl is monocyclic, i.e., phenyl. The alkyl chain includes both straight or branched chain radicals of 1 to 4 carbon atoms. "Heteroaryl" as used herein, is meant an aromatic ring system containing one or more heteroatoms, such as imidazolyl, triazolyl, oxalyl, pyridyl, pyrimidyl, pyrazolyl, pyrrolyl, furanyl, or thienyl. "Halo" as used herein is meant all halogens, i.e., chloro, fluoro, bromo, or iodo.

The phrase "inhibiting the production of IL-1" or "inhibiting the production of TNF" means:

a) a decree of excessive in vivo IL-1 or TNF levels, respectively, in a human to normal levels or below normal levels by inhibition of the in vivo release of IL-1 by all cells, including but not limited to monocytes or macrophages;

b) a down regulation, at the translational or transcriptional level, of excessive in vivo IL-1 or TNF levels, respectively, in a human to normal levels or below normal levels; or c) a down regulation, by inhibition of the direct synthesis of IL-1 or TNF levels as a postranslational event.

"TNF mediated disease or disease states" means any and all disease states in which TNF plays a role, either by production of TNF itself, or by TNF causing another cytokine to be released, such as but not limited to IL-1 or IL6. A disease state in which IL-1, for instance is a major component, and whose production or action, is exacerbated or secreted in response to TNF, would therefore be considered a disease state mediated by TNF. As TNF-β (also known as lymphotoxin) has close structural homology with TNF-α (also known as cachectin), and since each induces similar biologic responses and binds to the same cellular receptor, both TNF-α and TNF-β are inhibited by the compounds of the present invention and thus are herein referred to collectively as "TNF" unless specifically delineated otherwise. Preferably TNF-α is inhibited.

"Cytokine" means any secreted polypeptide that affects the functions of cells, and is a molecule which modulates interactions between cells in immune, inflammatory, or hematopoietic responses. A cytokine includes, but is not limited to, monokines and lymphokines regardless of which cells produce them. For instance, a monokine is generally referred to as being produced and secreted by a mononuclear cell, such as a macrophage and/or monocyte, but many other cells produce monokines, such as natural killer cells, fibroblasts, basophils, neutrophils, endothelial cells, brain astrocytes, bone marrow stromal cells, epidermal keratinocytes, and B-lymphocytes. Lymphokines are generally referred to as being produced by lymphocyte cells. Examples of cytokines for the present invention include, but are not limited to, Interleukin-1 (IL-1), Interleukin-6 (IL-6), Interleukin-8 (IL-8), Tumor Necrosis Factor-alpha (TNF-α) and Tumor Necrosis Factor-beta (TNF-β).

The cytokine inhibited by the present invention for use in the treatment of a HIV-infected human must be a cytokine which is implicated in (a) the initiation and/or maintenance of T cell activation and/or activated T cell-mediated HIV gene expression and/or replication, and/or (b) any cytokine-mediated disease associated problem such as cachexia or muscle degeneration. Preferably this cytokine is TNF-α.

All of the compounds of Formula (I) are useful in the method of inhibiting the production of TNF, preferably by macrophages, monocytes or macrophages and monocytes, in a mammal, including humans, in need thereof. All of the compounds of Formula (I) are useful in the method of inhibiting or mediating the enzymatic or catalytic activity of PDE IV and in treatment of disease states mediated thereby.

METHODS OF PREPARATION

Preparing compounds of Formula (I) can be carried out by one of skill in the art according to the procedures outlined in the Examples, infra. For example, reactioning a compound of Formula (2)

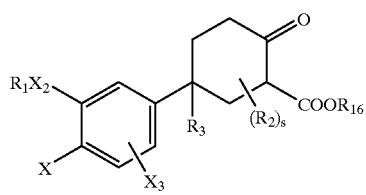

(2)

wherein X or $X_3$ is other than Br, I, $NO_2$, amino, or $S(O)_{m'}R_2$ when m' is 0, 1 or 2, $R_1$ represents $R_1$ as defined in relation to Formula (I) or a group convertable to $R_1$ and X, $X_2$ and $X_3$ represent X, $X_2$ and $X_3$ as defined in relation to Formula (I) or a group convertable to X, $X_2$ or $X_3$ and $R_3$ represents $R_3$ as defined in relation to Formula (I) or a group convertable to $R_3$ and $R_{16}$ is an allyl, phenyl or benzyl group with, e.g., trifluoromethanesulfonic anhydride in the presence of a suitable base, such as a hindered amine base, in a suitable solvent, such as dichloromethane, provides a compound of Formula (3)

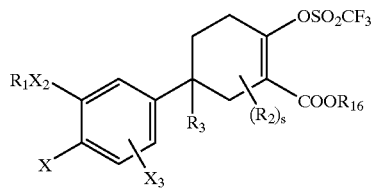

(3)

wherein X or $X_3$ is other than Br, I, $NO_2$, amino, or $S(O)_{m'}R_2$ when m' is 0, 1 or 2, $R_1$ represents $R_1$ as defined in relation to Formula (I) or a group convertable to $R_1$ and X, $X_2$ and $X_3$ represent X, $X_2$ and $X_3$ as defined in relation to Formula (I) or a group convertable to X, $X_2$ or $X_3$ and $R_3$ represents $R_3$ as defined in relation to Formula (I) or a group convertable to $R_3$ and $R_{16}$ is an alkyl, phenyl or benzyl group. Palladium-catalyzed reduction of such a compound of Formula (3) under suitable conditions then provides a compound of Formula (4)

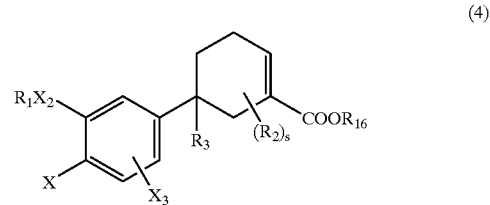

(4)

a subset of the compounds of Formula (1) wherein X or $X_3$ is other than Br, I, $NO_2$, amino, or $S(O)_{m'}R_2$ when m' is 0, 1 or 2, the double bond is present, $R_1$ represents $R_1$ as defined in relation to Formula (I) or a group convertable to $R_1$ and X, $X_2$ and $X_3$ represent X, $X_2$ and $X_3$ as defined in relation to Formula (I) or a group convertable to X, $X_2$ or $X_3$ and $R_3$ represents $R_3$ as defined in relation to Formula (I) or a group convertable to $R_3$ and $R_{16}$ is an alkyl, phenyl or benzyl group. Such compounds of Formula (1) wherein X or $X_3$ is other than Br, I, $NO_2$, amino, or $S(O)_{m'}R_2$ when m' is 0, 1 or 2, the double bond is present and Z is $COOR_{16}$ can be converted to other compounds of Formula (1) wherein X or $X_3$ is other than Br, I, $NO_2$, amino, or $S(O)_{m'}R_2$ when m' is 0, 1 or 2 and the double bond is present by standard procedures well known in the art [with proper manipulation (protection/deprotection) of any chemically sensitive functional groups, if necessary] to the corresponding ester, amide, nitrile, oxazolidinone, etc., Z groups of Formula (I) wherein X or $X_3$ is other than Br, I, $NO_2$, amino, or $S(O)_{m'}R_2$ when m' is 0, 1 or 2 and the double bond is present. Alternatively, such compounds of Formula (I) wherein X or $X_3$ is other than Br, I, $NO_2$, amino, or $S(O)_{m'}R_2$ when m' is 0, 1 or 2, the double bond is present, $R_1$ represents $R_1$ as defined in relation to Formula (I) or a group convertable to $R_1$ and X, $X_2$ and $X_3$ represent X, $X_2$ and $X_3$ as defined in relation to Formula (I) or a group convertable to X, $X_2$ or $X_3$ and $R_3$ represents $R_3$ as defined in relation to Formula (I) or a group convertable to $R_3$ and $R_{16}$ is an alkyl, phenyl or benzyl group may then be reduced by, e.g., catalytic hydrogenation, to compounds of Formula (I) wherein X or $X_3$ is other than Br, I, $NO_2$, amino, or $S(O)_{m'}R_2$ when m' is 0, 1 or 2 and the double bond is absent. Functional conversion of the Z group in such compounds of Formula (I) wherein X or $X_3$ is other than Br, I, $NO_2$, amino, or $S(O)_{m'}R_2$ when m' is 0, 1 or 2, the double bond is absent, $R_1$ represents $R_1$ as defined in relation to Formula (I) or a group convertable to $R_1$ and X, $X_2$ and $X_3$ represent X, $X_2$ and $X_3$ as defined in relation to Formula (I) or a group convertable to X, $X_2$ or $X_3$ and $R_3$ represents $R_3$ as defined in relation to Formula (I) or a group convertable to $R_3$ and $R_{16}$ is an alkyl, phenyl or benzyl group to other Z groups can be accomplished by standard procedures well known in the art [with proper manipulation (protection/deprotection) of any chemically sensitive functional groups, if necessary]. For example, preparation of some compounds of Formula (I) wherein $R_3$ is, e.g., C(=Z')H proceed in an analogous fashion from the compound of Formula (2) wherein =Z' is an aldehyde protecting group, such as a dimethylacetal or a dioxolane, followed by aldehyde deprotection and subsequent manipulation by standard procedures known to those of skill in the art to the remaining compounds of Formula (I). Likewise, isomerization of compounds of Formula (I) wherein X or $X_3$ is other than Br, I, $NO_2$, amino, or $S(O)_{m'}R_2$ when m' is 0, 1 or 2, the double bond is absent, $R_1$ represents $R_1$ as defined in relation to Formula (I) or a group convertable to $R_1$ and X, $X_2$ and $X_3$ represent X, $X_2$ and $X_3$ as defined in relation to Formula (I) or a group convertable to X, $X_2$ or $X_3$ and $R_3$ represents $R_3$ as defined in relation to Formula (I) or a group convertable to $R_3$ and $R_{16}$ is an ally, phenyl or benzyl group and the $R_3$ and Z groups are cis to the isomer wherein the $R_3$ and Z groups are trans can be accomplished either under kinetic or thermodynamic deprotonation conditions by standard procedures well known in the art with proper manipulation (protection/deprotection) of any chemically sensitive functional groups.

Alternatively, compounds of Formula (I) wherein X or $X_3$ is other than Br, I, $NO_2$, amino, or $S(O)_{m'}R_2$ when m' is 0, 1 or 2 may be prepared by a reaction sequence analogous to that described above but starting with a compound of Formula (5)

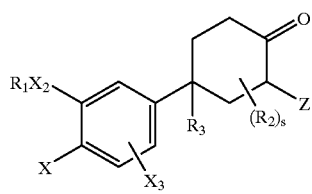

(5)

wherein X or $X_3$ is other than Br, I, $NO_2$, amino, or $S(O)m'$ when m' is 0, 1 or 2, the double bond is absent, $R_1$ represents $R_1$ as defined in relation to Formula (I) or a group convertable to $R_1$ and X, $X_2$ and $X_3$ represent X, $X_2$ and $X_3$ as defined in relation to Formula (I) or a group convertable to X, $X_2$ or $X_3$ and $R_3$ represents $R_3$ as defined in relation to Formula (I) or a group convertable to $R_3$ and Z represents Z as defined in relation to Formula (I) or a group convertable to Z.

Any remaining compounds of Formula (I) not described therein may be prepared by the analogous processes disclosed herein which comprise:

With proper manipulation (protection/deprotection) of any chemically sensitive functional groups:

a) Compounds of Formula (I) wherein X or $X_3$ are formyl amine may be formed at the last step, by formylating a compound wherein X or $X_3$ is $NH_2$, obtained by removal of a protecting group from the amine functionality; such protective groups are well known to those skilled in the art, See Greene, T. and Wuts, P. G. M., Protecting Groups in Organic Synthesis, 2nd Ed., John Wiley and Sons, New York (1991).

b) Compounds of Formula (I) wherein X or $X_3$ are Br, I or $SR_2$ may be prepared from a similarly deprotected amine by diazotization of the amine and diazonium displacement.

c) Compounds of Formula (I) wherein X or $X_3$ are $NO_2$ may be prepared from a similarly deprotected amine by oxidating the amine to the nitro group.

d) Compounds of Formula (I) wherein Y is S(O)m' when m' is 1 or 2 may be prepared from the compounds of Formula (I) wherein Y is S by first protecting any other oxidizable groups which are not to be oxidized then oxidizing the $SR_2$ moiety under conditions well known those skilled in the art and then deprotecting the previously protected group.

Compounds of Formulas (2) and (5) may be prepared in turn by the processes described in co-pending applications described in PCT applications PCT/US93/02230, and its predecessor applications PCT/US93/02046, U.S. Ser. No. 07/968,806 filed Oct. 30, 1992 and U.S. Ser. No. 07/862,114 filed Apr. 2, 1992; and PCT application PCT/US93/10325 filed Mar. 12, 1993 and the predecessor cases from which priority is claimed therein.

Alternatively, reacting a compound of the Formula (6)

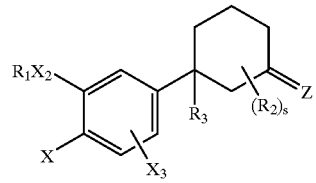

(6)

wherein $R_1$ represents $R_1$ as defined in relation to Formula (I) or a group convertable to $R_1$ and X, $X_2$ and $X_3$ represent X, $X_2$ and $X_3$ as defined in relation to Formula (I) or a group convertable to X, $X_2$ or $X_3$ and $R_2$ and $R_3$ represent $R_2$ and $R_3$ as defined in relation to Formula (I) or a group convertable to $R_2$ or $R_3$ and wherein X or $X_3$ is other than Br, I, $NO_2$, amino, or $S(O)_{m'}R_2$ when m' is 0, 1 or 2 and $R_3$ is other than C(=Z')H, with a suitable base in a suitable non-reacting solvent followed by reaction with a suitable acylating agent, such as $LS(O)_2CF_3$, wherein L is a leaving group, to provide compounds of the Formula (7)

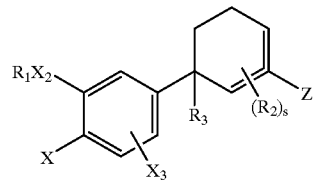

(7)

wherein Z is $S(O)_2CF_3$ and $R_3$ is other than C(=Z')H. Metal catalyzed carboxymethylation of such compounds of the Formula (7) then provides the compounds of the Formula (I) wherein Z is $COOR_{16}$, which may be converted to other compounds of the formula (1) as described above. Preparation of such compounds of Formula (I) wherein $R_3$ is C(=Z')H proceeds in an analogous fashion from the compound of Formula (6) wherein =Z' is an aldehyde protecting group, such as a dimethylacetal or a dioxolane, followed by deprotection to the aldehyde at the end of the reaction sequence and subsequent elaboration by standard procedures known to those of skill in the art to the remaining compounds of Formula (1) wherein Z' is other than O.

Compounds of the Formula (6) may be prepared in turn by processes described in co-pending application U.S. Ser. No. 08/130,215 filed Oct. 1, 1993. P50199.

It will be recognized that compounds of Formula (I) may exist in two distinct diastereomeric forms possessing distinct physical and biological properties; such isomers may be separated by standard chromatographic methods.

The following examples and methods are provided to illustrate how the make and use the invention. These materials are not intended to limit the invention in any manner, please refer to the claims appended hereto for determining what has been reserved to the inventors hereunder.

EXAMPLES

Example 1

Preparation of methyl 5-cyano-5-(3-cyclopropylmethoxy-4-methoxyphenyl)cyclohex-1-ene-1-carboxylate, SB 212179

Route A

1a) Methyl 5-cyano-5-(3-cyclopropylmethoxy-4-methoxyphenyl)-2-(trifluoromethylsulfonato)-cyclohex-1-ene-1-carboxylate To a solution of 2,6-di-tert-butyl-4-methylpyridine (10.3 grams [hereinafter g], 50.2 millimoles [hereinafter mmol] and trifluoromethanesulfonic anhydride (7.07 milliliters [hereinafter mL], 41.8 mmol) in dichloromethane (165 mL) at room temperature under an argon atmosphere was added over 0.5 hours [hereinafter h] a solution of 2-carbomethoxy-4-cyano-4-(3-cyclopropylmethoxy-4-methoxyphenyl)cyclohexan-1-one (12 g, 33.6 mmol) in dichloromethane (160 mL). The resulting mixture was stirred overnight and then was concentrated to half-volume. Ether was added, the salt was removed by filtration and the filtrate was concentrated in vacuo. Purification by flash chromatography, eluting with 3:1 hexanes/ethyl acetate, afforded a yellow oil (14.7 g, 89%). $^1$H NMR (400 MHz, CDCl$_3$) δ7.0 (dd, J=8.5 and 2 Hz, 1H), 6.95 (d, J=2 Hz, 1H), 6.90 (d, J=8.5 Hz, 1H), 3.85 (m, 8H), 3.10 (AB system, J=15 Hz, 2H), 2.88 (m, 1H), 2.56 (m, 1H), 2.33 (m, 2H), 1.35 (m, 1H), 0.67 (dt, J=7 and 7 Hz, 2H), 0.49 (dt, J=7 and 7 Hz, 2H).

1b) Methyl 5-cyano-5-(3-cyclopropylmethoxy-4-methoxyphenyl)cyclohex-1-ene-1-carboxylate To a mixture of methyl 5-cyano-5-(3-cyclopropylmethoxy-4-methoxyphenyl)-2-(trifluoromethylsulfonato)cyclohex-1-ene-1-carboxylate (0.34 g, 0.69 mmol), triphenylphosphine (7.2 mg, 0.03 mmol), palladium acetate (3 mg, 0.013 mmol) and tributylamine (0.49 mL, 2.06 mmol) in N,N-dimethylformamide (1.5 mL) was added dropwise formic acid (0.054 mL, 1.37 mmol). The resulting mixture was heated at 60° C. under an argon atmosphere for 1 h. The mixture was poured into 2 N hydrochloric acid and was extracted twice with ethyl acetate. The organic extract was washed twice with 2 N hydrochloric acid, once with aqueous sodium bicarbonate, once with brine and was evaporated. Purification by flash chromatography, eluting with 4:1 hexanes/ethyl acetate, provided an oil. Anal. (C$_{20}$H$_{23}$NO$_4$.3/4 H$_2$O) calcd: C, 67.68; H, 6.96; N, 3.95; found: C, 67.50; H, 6.78; N 3.80.

Route B:

1c) 3-(3-Cyclopentyloxy-4-methoxyphenyl)cyclohex-2-en-1-one n-Butyllithium (2.5M in hexanes, 15.5 mL, 38.9 mmol) was added dropwise over 30 min to a solution of 3-cyclopentyloxy-4-methoxybromobenzene (10 g, 37 mmol,) in dry tetrahydrofuran (100 mL) at −78° C. under an argon atmosphere. After 1.5 h. this solution was cannulated into a solution of 3-methoxycyclohex-2-enone (4.62 g, 37.4 mmol, prepared as in Pearson, A. J.; Richards, I. C.; Gardner, D. V. J. Org. Chem. 1984, 49, 3887–3891) in dry tetrahydrofuran (50 mL) at 0° C. under an argon atmosphere. After 2 h at room temperature, a mixture of ether and water was added, the aqueous layer was twice more extracted with ether, the combined extract was washed with water and brine, was dried (magnesium sulfate) and was evaporated. Trituration from ether/hexanes provided an off-white solid (7.33 g, 68%). Further purification of the mother liquor by flash chromatography, eluting with 1:3 ethyl acetate/ hexanes, followed by trituration from ether/hexanes, provided a white solid (1.59 g, 7%). mp 89–90° C.; Anal. (C$_{18}$H$_{22}$O$_3$.1/8 H$_2$O) calcd: C, 74.91; H, 7.77; found: C, 74.96; H, 7.76.

1d) 3-Cyano-3-(cyclopentyloxy-4-methoxyphenyl)cyclohexan-1-one

To a solution of 3-(3-cyclopentyloxy-4-methoxyphenyl)cyclohex-2-en-1-one (1.46 g, 5.10 mmol) in dry toluene (45 mL) at room temperature under an argon atmosphere was added over 5 min diethylaluminumcyanide (1.0 M solution in toluene, 15.5 mL, 15.5 mmol). After 6 h, the reaction was carefully quenched with sodium hydroxide (2 N, 75 mL, 150 mmol), was extracted three times with methylene chloride, the extract was dried (magnesium sulfate) and was evaporated. Purification by flash chromatography, eluting with 1:4 ethyl acetate/hexanes, provided a pale yellow solid (1.20 g, 75%). mp 110–111° C.; Anal. (C$_{19}$H$_{23}$NO$_3$.1/8 H$_2$O) calcd: C, 72.30; H, 7.42; N, 4.44; found: C, 72.24; H, 7.45; N, 4.58.

1e) Methyl 3-cyano-3-(3-cyclopentyloxy-4-methoxyphenyl)cyclohex-1-ene-1-carboxylate and methyl 5-cyano-5-(3-cyclopentyloxy-4-methoxyphenyl)cyclohex-1-ene-1-carboxylate A mixture of 3-cyano-3-(3-cyclopentyloxy-4-methoxyphenyl)-cyclohex-1-en-1-yl trifluoromethanesulfonamide and 5-cyano-5-(3-cyclopentyloxy-4-methoxyphenyl)cyclohex-1-en-1-yl trifluoromethanesulfonamide (15.9 g, 35.7 mmol), triphenylphosphine (1.87 g, 7.14 mmol), palladium acetate (400 mg, 1.79 mmol) and tributylamine (25.5 mL, 107 mmol) in methanol (300 mL) was saturated with carbon monoxide, then stirred under a carbon monoxide balloon for 4 days. The solvent was evaporated, the residue was diluted with water and was extracted three times with dichloromethane, was dried (magnesium sulfate) and was evaporated. Purification by flash chromatography, eluting with 85:15 hexanes/ethyl acetate, provided a white, waxy solid (6.21 g, 51%, R$_f$=0.36 (2:8 ethyl acetate:hexanes)). Also isolated was the isomer: methyl 3-cyano-3-(3-cyclopentyloxy-4-methoxyphenyl)cyclohex-1-ene-1-carboxylate as a colorless oil (5.01 g, 39%, R$_f$=0.43 (2:8 ethyl acetate:hexanes)).

1f) Methyl cis-[3-cyano-3-(3-cyclopentyloxy-4-methoxyphenyl)cyclohexane-1-carboxylate]

To a solution of methyl 5-cyano-5-(3-cyclopentyloxy-4-methoxyphenyl)-cyclohex-1-ene-1-carboxylate (6.21 g, 17.5 mmol) in methanol (50 mL) was added 10% palladium on activated carbon (0.60 g) and the resulting mixture was hydrogenated at 50 psi for 5 h. The mixture was filtered though a pad of Celite®, the solid was washed with dichloromethane and the filtrate was concentrated under reduced pressure. Purification by flash chromatography, eluting with 85:15 hexanes:ethyl acetate, provided methyl cis-[3-cyano-3-(3-cyclopentyloxy-4-methoxyphenyl)cyclohexane-1-carboxylate] as a colorless oil (5.60 g, 90%).

Alternatively, to a solution of methyl 3-cyano-3-(3-cyclopentyloxy-4-methoxyphenyl)cyclohex-1-ene-1-carboxylate (0.10 g, 0.28 mmol) in methanol (10 mL) was added 10% palladium on activated carbon (0.05 g) and the resulting mixture was hydrogenated at 50 psi for 6 h. The mixture was filtered through a pad of Celite®, the solid was washed with dichloromethane and the filtrate was concentrated under reduced pressure. Purification by flash chromatography, eluting with 9:1 hexanes:ethyl acetate, provided methyl cis-[3-cyano-3-(3-cyclopentyloxy-4-methoxyphenyl)cyclohexane-1-carboxylate] as a colorless oil (0.04 g, 43%). Also isolated was unreacted starting material (0.04 g, 42%).

Example 2

Preparation of ethyl 5cyano-5-(3-cyclopropylmethoxy-4-methoxyphenyl)cyclohex-1-ene-1-carboxylate, SB Following the procedure of Example 1(a)–1(b), except substituting 2-carboethoxy-4-cyano-4-(3-cyclopropylmethoxy-4-methoxyphenyl)cyclohexan-1-one for 2-carbomethoxy-4-cyano-4-(3-cyclopropylmethoxy-4-methoxyphenyl)cyclohexan-1-one, the title compound was prepared as an oil (0.57 g, 95%).

Example 3

Preparation of methyl 5cyano-5-(3-cyclopentyloxy-4-methoxyphenyl)cyclohex-1-ene-1-carboxylate, SB 211572

Following the procedure of Example 1(a)–1(b), except substituting 2-carbomethoxy-4-cyano-4-(3-cyclopentyloxy- 4-methoxyphenyl)cyclohexan-1-one for 2-carbomethoxy-4-cyano-4-(3-cyclopropylmethoxy-4-methoxyphenyl)cyclohexan-1-one, the title compound was prepared as a white solid (0.23 g, 54%). mp 68–71° C.; Anal. ($C_{21}H_{25}NO_4 \cdot 1/2\ H_2O$) calcd: C, 69.40; H, 6.93; N, 3.85; found: C, 69.48; H, 7.33; N, 3.69.

Example 4

Preparation of methyl-5-(3,4-bisdifluoromethoxyphenyl)-5-cyanocyclohex-1-ene-1-carboxylate, SB Following the procedure of Example 1(a)–1(b), except substituting 2-carbomethoxy-4-(3,4-bisdifluoromethoxyphenyl)-4-cyanocyclohexan-1-one for 2-carbomethoxy-4-cyano-4-(3-cyclopropylmethoxy-4-methoxyphenyl)cyclohexan-1-one, the title compound was prepared (0.10 g, 51%). $^1$H NMR (400 MHz, $CDCl_3$) δ7.41 (dd, J=8.5 and 2 Hz, 1H), 7.38 (d, J=2 Hz, 1H), 7.32 (d, J=8.5 Hz, 1H), 7.17 (m, 1H), 6.56 (t, J=73 Hz, 1H), 6.55 (t, J=73 Hz, 1H), 3.78 (s, 3H), 2.86 (AB system, J=18 Hz, 2H), 2.70 (m, 1H), 2.52 (m, 1H), 2.24 (m, 1H), 2.04 (m, 1H).

Example 5

Preparation of methyl cis-[3-cyano-3-(3-cyclopropylmethoxy-4-methoxyphenyl)cyclohexane-1-carboxylate], SB 210667

To a solution of methyl 5-cyano-5-(3-cyclopropylmethoxy-4-methoxyphenyl)cyclohex-1-ene-1-carboxylate (0.4 g, 1.17 mmol) in methanol (10 mL) was added 10% palladium on activated carbon (0.15 g) and the resulting mixture was hydrogenated at 50 psi for 3 h. The mixture was filtered through a pad of Celite®, the solid was washed with dichloromethane and the filtrate was concentrated under reduced pressure. Purification by flash chromatography, eluting with 3:1 hexanes/ethyl acetate, provided a colorless oil (0.27 g, 67%). Anal. ($C_{20}H_{25}NO_4$) calcd: C, 69.95; H, 7.34; N, 4.08; found: C, 69.74; H, 7.17; N, 4.06.

Example 6

Preparation of ethyl cis-[3-cyano-3-(3-cyclopropylmethoxy-4-methoxyphenyl)cyclohexane-1-carboxylate], SB 211600

Following the procedure of Example 5, except substituting ethyl 5-cyano-5-(3-cyclopropylmethoxy-4-methoxyphenyl)cyclohex-1-ene-1-carboxylate for methyl 5-cyano-5-(3-cyclopropylmethoxy-4-methoxyphenyl)cyclohex-1-ene-1-carboxylate, the title compound was prepared (0.43 g, 75%). Anal. ($C_{21}H_{27}NO_4 \cdot 1/8\ H_2O$) calcd: C, 70.12; H, 7.64; N, 3.89; found: C, 70.11; H, 7.58; N, 4.23.

Example 7

Preparation of methyl cis-[3-cyano-3-(3-cyclopentyloxy-4-methoxyphenyl)cyclohexane-1-carboxylate], SB 212066

Following the procedure of Example 5, except substituting methyl 5-cyano-5-(3-cyclopentyloxy-4-methoxyphenyl)cyclohex-1-ene-1-carboxylate for methyl 5-cyano-5-(3-cyclopropylmethoxy-4-methoxyphenyl)cyclohex-1-ene-1-carboxylate, the title compound was prepared as a colorless oil (0.1 g, 67%). Anal. ($C_{21}H_{27}NO_4 \cdot 1/2\ H_2O$) calcd: C, 68.83; H, 7.70; N, 3.82; found: C, 68.83; H, 7.49; N, 3.63.

Example 8

Preparation of methyl cis-[3-(3,4-bisdifluoromethoxyphenyl)-3-cyanocyclohexane-1-carboxylate, SB Following the procedure of Example 5, except substituting methyl 5-cyano-5-(3,4-bisdifluoromethoxyphenyl)cyclohex-1-ene-1-carboxylate for methyl 5-cyano-5-(3-cyclopropylmethoxy-4-methoxyphenyl)cyclohex-1-ene-1-carboxylate, the title compound was prepared.

Example 9

Preparation of cis-[3-cyano-3-(3-cyclopropylmethoxy-4-methoxyphenyl)cyclohexane-1-carboxylic acid] and separation of the 1R,3S- and 1S,3R-enantiomers, SB 210984

To a solution of methyl cis-[3-cyano-3-(3-cyclopropylmethoxy-4-methoxyphenyl)cyclohexane-1-carboxylate] (0.2 g, 0.58 mmol) in methanol (5.8 mL) under an argon atmosphere was added a solution of potassium hydroxide (0.098 g, 1.5 mmol) in water (3.4 mL). The resulting mixture was stirred at room temperature overnight, then poured into acidic water and extracted three times with ethyl acetate. The extract was dried (magnesium sulfate) and concentrated under reduced pressure. Purification by flash chromatography, eluting with 5% methanol/chloroform, provided a foam (0.16 g, 84%). Anal. ($C_{19}H_{23}NO_4 \cdot 1/8H_2O$) calcd: C, 68.81; H, 7.07; N, 4.22; found: C, 68.81; H, 7.17; N, 4.26. Chiral separation of cis-[3-cyano-3-(3-cyclopropylmethoxy-4-methoxyphenyl)cyclohexane-1-carboxylic acid] was accomplished using preparative HPLC conditions with a 21.2×250 mm Chiralpak AD column. The mobile phase of 85:15:0.2 hexanes:isopropanol/water eluted at a flow rate of 10 mL/min with injection of 0.1 g/10 mL at ambient temperature. Ultraviolet detection of the eluting product was employed at 294 nm. Retention times were 26.3 min for the 1R,3S-isomer and 34.2 min for the 1S,3R-isomer.

Example 10

Preparation of cis-[3-cyano-3-(3-cyclopentyloxy) cyclohexane-1-carboxylic acid], SB 212510

Following the procedure of Example 9, except substituting methyl cis-[3-cyano-3-(3-cyclopentyloxy-4-methoxyphenyl)cyclohexane-1-carboxylate] for methyl cis-[3-cyano-3-(3-cyclopropylmethoxy-4-methoxyphenyl) cyclohexane-1-carboxylate] and using a solvent mixture of 5:5:2 tetrahydrofuran/methanol/water, the title compound was prepared as a white solid (0.02 g, 78%). mp 48–50° C.; Anal. ($C_{20}H_{25}NO_4 \cdot 5/4\ H_2O$) calcd: C, 66.05; H, 7.55; N, 3.85; found: C, 65.98; H, 7.71; N, 4.21.

Example 11

Preparation of cis-[3-cyano-3-(3-cyclopropylmethoxy-4-methoxyphenyl)cyclohexane-1-carboxamide] SB 211529

A solution of cis-[3-cyano-3-(3-cyclopropylmethoxy-4-methoxyphenyl)cyclohexane-1-carboxylic acid] (0.1 g, 0.3 mmol) and N-methylmorpholine (0.04 mL, 0.36 mmol) in 1,2-dimethoxyethane (3.2 mL) at room temperature under an argon atmosphere was treated with isobutyl chloroformate (0.045 mL 0.35 mmol). After 15 min. concentrated ammonium hydroxide (6 drops) was added and the mixture was stirred for an additional 0.5 h. The mixture was partitioned between dichloromethane and 5% aqueous sodium bicarbonate, was extracted three times, the organic extract was dried (potassium carbonate) and the solvent was evaporated. Purification by flash chromatography, eluting with 5% methanol/chloroform, provided a foam (0.05 g, 51%). This material was combined with the product of a reaction conducted on a similar scale and was rechromatographed. Anal. ($C_{19}H_{24}N_2O_3 \cdot 1/2H_2O$) calcd: C, 67.63; H, 7.47; N, 8.30; found: C, 67.59; H, 7.28; N, 8.04.

Example 12

Preparation of cis-[3-cyano-3-(3-cyclopropylmethoxy-4-methoxyphenyl)cyclohexane-1-N-methylcarboxamide] SB 213021

Following the procedure of Example 11, except substituting methylamine hydrochloride for ammonium hydroxide and using a four-fold excess of N-methylmorpholine, the title compound was prepared as a foam. Anal. ($C_{20}H_{26}N_2O_3 \cdot 1/2H_2O$) calcd: C, 68.35; H, 7.74; N, 7.97; found: C, 68.27; H, 7.70; N, 7.91.

Example 13

Preparation of cis-[3-cyano-3-(3-cyclopropylmethoxy-4-methoxyphenyl)cyclohexane-1-N,N-dimethylcarboxamide] SB 212697

Following the procedure of Example 11, except substituting dimethylamine hydrochloride for ammonium hydroxide, the title compound was prepared as a white solid. mp 105° C.; Anal. ($C_{21}H_{28}N_2O_3 \cdot 1/4H_2O$) calcd: C, 69.88; H, 7.96; N, 7.76; found: C, 69.72; H, 7.78; N, 7.74.

Example 14

Preparation of cis-[3-cyano-3-(3-cyclopropylmethoxy-4-methoxyphenyl)cyclohexane-1-{N-(4-bromobenzyl)carboxamide}] SB 212698

Following the procedure of Example 11, except substituting 4-bromobenzyl amine hydrochloride for ammonium hydroxide and using a four-fold excess of N-methylmorpholine, the title compound was prepared as a white solid. mp 162–163° C.; Anal ($C_{26}H_{29}BrN_2O_3 \cdot 1/2H_2O$) calcd: C, 61.66; H, 5.97; N 5.53; found: C, 61.66; H, 5.89; N, 5.57.

Example 15

Preparation of cis-[3-cyano-3-(3-cyclopentyloxy-4-methoxyphenyl)cyclohexane-1-carboxamide] SB 214236

Following the procedure of Example 11, except substituting cis-[3-cyano-3-(3-cyclopentyloxy-4-methoxyphenyl)cyclohexane-1-carboxylic acid] for cis-[3-cyano-3-(3-cyclopropylmethoxy-4-methoxyphenyl)cyclohexane-1-carboxylic acid], the title compound was prepared as a white solid (0.6 g, 98%). mp 145–146° C.; Anal. ($C_{20}H_{26}N_2O_3 \cdot 1/8H_2O$) calcd: C, 69.69; H, 7.68; N, 8.13; found: C, 69.53; H, 7.64; N, 8.03.

Example 16

Preparation of cis-[3-(3-cyclopropylmethoxy-4-methoxyphenyl)-1,3-dicyanocyclohexane] SB 212188

A solution of cis-[3-cyano-3-(3-cyclopropylmethoxy-4-methoxyphenyl)cyclohexane-1-carboxamide] (0.29 g, 0.87 mmol) and pyridine (0.15 mL, 1.86 mmol) in tetrahydrofuran (5 mL) at room temperature under an argon atmosphere was treated with trifluoroacetic anhydride (0.13 mL, 0.92 mmol). After stirring for 2.5 h, saturated aqueous ammonium chloride was added and the mixture was partitioned between ethyl acetate and 10% hydrochloric acid. The aqueous layer was extracted three times, the organic extract was dried (magnesium sulfate) and evaporated. Purification by flash chromatography, eluting with 2:1 hexanes/ethyl acetate, provided a solid (0.19 g, 71%). mp 138.5–139° C.; Anal. ($C_{19}H_{22}N_2O_2$) calcd: C, 73.52; H, 7.14; N, 9.03; found: C, 73.63; H, 7.15; N, 8.84.

Example 17

Preparation of cis-[3-(3-cyclopentyloxy-4-methoxyphenyl)-1,3-dicyanocyclohexane] SB 213832

Following the procedure of Example 16, except substituting cis-[3-cyano-3-(3-cyclopentyloxy-4-methoxyphenyl)cyclohexane-1-carboxamide] for cis-[3-cyano-3-(3-cyclopropylmethoxy-4-methoxyphenyl)cyclohexane-1-carboxamide], the title compound was prepared as a white solid (0.18 g, 71%). mp 113–115° C.; Anal. ($C_{20}H_{24}N_2O_2$) calcd: C, 74.05; H, 7.46; N, 8.63; found: C, 73.96; H, 7.42; N, 8.64.

Example 18

Preparation of cis-[3-cyano-3-(3-cyclopropylmethoxy-4-methoxyphenyl)-1-(3-methyl[1,2,4]oxadiazol-5-yl)cyclohexane] SB 213826

A solution of cis-[3-cyano-3-(3-cyclopropylmethoxy-4-methoxyphenyl)cyclohexane-1-carboxamide] (0.097 g, 0.30 mmol) in N,N-dimethylacetamide dimethyl acetal (1.2 mL) was heated at 110° C. under an argon atmosphere for 1 h, was cooled and the solvent was evaporated. Dioxane (1.2 mL), acetic acid (1.2 mL), hydroxylamine hydrochloride (0.03 g, 0.42 mmol) and 10% aqueous sodium hydroxide (0.18 mL, 0.45 mmol) were added and the mixture was heated at 90° C. under an argon atmosphere for 2 h. The mixture was cooled, water was added, the mixture was extracted three times with methylene chloride, the organic extract was dried (magnesium sulfate) and was evaporated. Purification by flash chromatography, eluting with 35% ethyl acetate/hexanes, provided an oil (0.06 g, 55%). Anal. ($C_{21}H_{25}N_3O_3 \cdot 1/4\,H_2O$) calcd: C, 67.81; H, 6.91; N, 11.30; found: C, 67.73; H, 6.98; N, 11.14.

Example 19 preparation of cis-{3-cyano-3-(3-cyclopentyloxy-4-methoxyphenyl)-1-(3-methyl[1,2,4]-oxadiazol-5-yl)cyclohexane} SB 214243

Following the procedure of Example 18, except substituting cis-[3-cyano-3-(3-cyclopentyloxy-4-methoxyphenyl)cyclohexane-1-carboxamide] for cis-[3-cyano-3-(3-cyclopropylmethoxy-4-methoxyphenyl)cyclohexane-1-carboxamide], the title compound was prepared as a colorless oil (0.29 g, 66%). Anal. ($C_{22}H_{27}N_3O_3 \cdot 1/2\,H_2O$) calcd: C, 67.67; H, 7.23; N, 10.76; found: C, 67.72; H, 6.94; N, 10.52.

Example 20

Preparation of methyl trans-[3-cyano-3-(3-cyclopropylmethoxy-4-methoxyphenyl)cyclohexane-1-carboxylate], SB 213677

A solution of methyl cis [3-cyano-3-(3-cyclopropylmethoxy-4-methoxyphenyl)cyclohexane-1- carboxylate] (0.82 g, 2.39 mmol) in N-methylpyrrolidinone (10 mL) was treated with sodium cyanide (0.12 g, 2.51 mmol) and heated at 90° C. under an argon atmosphere for 6 h. The mixture was cooled, water (30 mL) was added, the mixture was extracted once with ether, once with ethyl acetate, the combined extract was washed with water, was dried (magnesium sulfate) and was evaporated. Purification by flash chromatography, eluting with 3:1 hexanes/ethyl acetate, provided an oil (0.41 g, 50%). Anal. ($C_{20}H_{25}NO_4 \cdot 1/8 H_2O$) calcd: C, 69.49; H, 7.36; N, 4.05; found: C, 69.45; H, 7.20; N, 4.14.

Example 21

Preparation of methyl trans-[3-cyano-3-(3-cyclopentyloxy-4-methoxyphenyl)cyclohexane-1-carboxylate], SB 213951

Following the procedure of Example 20, except substituting methyl cis-[3-cyano-3-(3-cyclopentyloxy-4-methoxyphenyl)cyclohexane-1-carboxylate] for methyl cis-[3-cyano-3-(3-cyclopropylmethoxy-4-methoxyphenyl) cyclohexane-1-carboxylate], the title compound was prepared (0.19 g, 40%). Anal. ($C_{21}H_{27}NO_4 \cdot 3/4\ H_2O$) calcd: C, 67.99; H, 7.74; N, 3.76; found: C, 68.07; H, 7.50; N, 4.09.

Example 22

Preparation of trans-[3-cyano-3-(3-cyclopropylmethoxy-4-methoxyphenyl)cyclohexane-1-carboxylic acid], SB 213731

Following the procedure of Example 9, except substituting methyl trans-[3-cyano-3-(3-cyclopropylmethoxy-4-methoxyphenyl)cyclohexane-1-carboxylate] for methyl cis-[3-cyano-3-(3-cyclopropylmethoxy-4-methoxyphenyl) cyclohexane-1-carboxylate], the title compound was prepared (0.17 g, 90%). Anal. ($C_{19}H_{22}NO_4 \cdot Na$) calcd: C, 64.95; H, 6.31; N, 3.99; found: C, 65.01; H, 6.51; N, 3.85.

Example 23

Preparation of trans-[3-cyano-3-(3-cyclopentyloxy-4-methoxyphenyl)cyclohexane-1-carboxylic acid], SB 213921

Following the procedure of Example 9, except substituting methyl trans-[3-cyano-3-(3-cyclopentyloxy-4-methoxyphenyl)cyclohexane-1-carboxylate] for methyl cis-[3-cyano-3-(3-cyclopropylmethoxy-4-methoxyphenyl) cyclohexane-1-carboxylate] and using a solvent mixture of 5:5:2 tetrahydrofuran/methanol/water, the title compound was prepared (0.075 g, 84%). Anal. ($C_{20}H_{25}NO_4 \cdot 1/2\ H_2O$) calcd: C, 68.16; H, 7.44; N, 3.97; found: C, 67.84; H, 7.23; N, 4.13.

Example 24

Preparation of trans-[3-cyano-3-(3-cyclopropylmethoxy-4-methoxyphenyl)cyclohexane-1-carboxamide] SB 213835

A solution of trans[3-cyano-3-(3-cyclopropylmethoxy-4-methoxyphenyl)cyclohexane-1-carboxylic acid] (0.19 g, 0.58 mmol) and triethylamine (0.10 mL, 0.70 mmol) in dichloromethane (5.0 mL) at 0° C. under an argon atmosphere was treated with isobutyl chloroformate (0.083 mL, 0.70 mmol). After 10 min., anhydrous ammonia was condensed into the reaction mixture and the mixture was stirred for an additional 0.5 h while warming to room temperature. The mixture was partitioned between 95:5 dichloromethane/methanol and 5% aqueous sodium carbonate, was extracted three times, the organic extract was dried (magnesium sulfate) and the solvent was evaporated. The residue was recrystallized from ethyl acetate/hexanes to provide a white solid (0.14 g, 76%). mp 174–176° C.; Anal. ($C_{19}H_{24}N_2O_3$) calcd: C, 69.49; H, 7.37; N, 8.53; found: C, 69.19; H, 7.38; N, 8.59.

Example 25

Preparation of trans-[3-cyano-3-(3-cyclopentyloxy-4-methoxyphenyl)cyclohexane-1-carboxamide] SB 213921

Following the procedure of Example 11, except substituting trans-[3-cyano-3-(3-cyclopentyloxy-4-methoxyphenyl)cyclohexane-1-carboxylic acid] for cis-[3-cyano-3-(3-cyclopropylmethoxy-4-methoxyphenyl) cyclohexane-1-carboxylic acid], the title compound was prepared as a white solid (0.65 g, 95%). mp 150–151° C.; Anal. ($C_{20}H_{26}N_2O_3$) calcd: C, 70.15; H, 7.65; N, 8.18; found: C, 69.90; H, 7.66; N, 8.04.

Example 26

Preparation of trans-[3-(3-cyclopropylmethoxy-4-methoxyphenyl)-1,3-dicyanocyclohexane] SB 213920

Following the procedure of Example 16, except substituting trans-[3-cyano-3-(3-cyclopropylmethoxy-4-methoxyphenyl)cyclohexane-1-carboxamide] for cis-[3-cyano-3-(3-cyclopropylmethoxy-4-methoxyphenyl) cyclohexane-1-carboxamide], the title compound was prepared (0.10 g, 92%). Anal. ($C_{19}H_{22}N_2O_2$) calcd: C, 73.52; H, 7.16; N, 9.03; found: C, 73.34; H, 7.16; N, 9.02.

Example 27

Preparation of trans-[3-(3-cyclopentyloxy-4-methoxyphenyl)-1,3-dicyanocyclohexane] SB 214241

Following the procedure of Example 16, except substituting trans-[3-cyano-3-(3-cyclopentyloxy-4-methoxyphenyl)cyclohexane-1-carboxamide] for cis-[3-cyano-3-(3-cyclopropylmethoxy-4-methoxyphenyl) cyclohexane-1-carboxamide], the title compound was prepared as a white solid (0.16 g, 66%). mp 118–119° C.; Anal. ($C_{20}H_{24}N_2O_2 \cdot 1/8\ H_2O$) calcd: C, 73.53; H, 7.48; N, 8.58; found: C, 73.47; H, 7.44; N, 8.46.

Example 28

Preparation of trans-{3-cyano-3-(3-cyclopentyloxyphenyl)-1-(3-methyl[1,2,4]oxadiazol-5-yl)cyclohexane}SB 214242

Following the procedure of Example 18, except substituting trans-[3cyano-3-(3-cyclopropylmethoxy-4-methoxyphenyl)cyclohexane-1-carboxamide] for cis-[3-cyano-3-(3-cyclopropylmethoxy-4-methoxyphenyl) cyclohexane-1-carboxamide], the title compound was prepared as a colorless oil (0.21 g, 70%). Anal. ($C_{22}H_{27}N_3O_3 \cdot 3/2\ H_2O$) calcd: C, 64.69; H, 7.03; N, 10.29; found: C, 64.98; H, 6.76; N, 9.90.

Example 29

Preparation of 5-(3-cyclopentyloxy-4-methoxyphenyl)cyclohex-1-ene-1,5-dicarbonitrile A suspension of 3-cyano-3-(cyclopentyloxy-4-methoxyphenyl)cyclohexan-1-one (0.63 g, 2.0 mmol), 18-crown-6 (0.006 g, 0.1 mmol) and potassium cyanide (0.006 g, 0.1 mmol) in dry toluene (2 mL) at room temperature under an argon atmosphere was treated dropwise with trimethylsilyl cyanide (0.32 mL, 2.4 mmol) and the mixture was stirred for 2.5 h. Pyridine (4 mL) and phosphorous oxychloride (0.5 mL, 5.0 mmol) were added, and the solution was refluxed for 40 h. After quenching with ice, the reaction was extracted three times with methylene chloride, the extract was washed with sodium bicarbonate, 10% hydrochloric acid and water, was dried (magnesium sulfate) and the solvent was evaporated. Purification by flash chromatography, eluting with 1:4 ethyl acetate/hexanes, provided a pale yellow oil (0.3 g, 42%). Anal. ($C_{20}H_{22}N_2O_2 \cdot 3/8H_2O$) calcd: C, 72.98; H, 6.97; N, 8.51; found: C, 72.85; H, 6.80; N, 8.56; $R_f$=0.13 (4:1 hexanes/ethyl acetate).

Example 30

Preparation of 3-(3-cyclopentyloxy-4-methoxyphenyl)cyclohex-1-ene-1,3-dicarbonitrile The title compound was isolated as the second product in Example 29 as an off-white solid (0.1 g, 19%). mp 77–79° C.; Anal. ($C_{20}H_{22}N_2O_2 \cdot 1/4H_2O$) calcd: C, 73.48; H, 6.94; N, 8.57; found: C, 73.19; H, 6.74; N, 8.34; $R_f$=0.32 (4:1 hexanes/ethyl acetate).

Methods of Treatment

In order to use a compound of Formula (I) or a pharmaceutically acceptable salt thereof for the treatment of humans and other mammals, it is normally formulated in accordance with standard pharmaceutical practice as a pharmaceutical composition. The compounds of Formula (I) or a pharmaceutically acceptable salt thereof can be used in the manufacture of a medicament for the prophylactic or therapeutic treatment of any disease state in a human or other mammal which is mediated by inhibition of PDE IV, such as but not limited to asthmas allergic, or inflammatory diseases. The compounds of Formula (I) are administered in an amount sufficient to treat such a disease in a human or other mammal.

The method of treatment and monitoring for an HIV-infected human manifesting immune dysfunction or cytokine-mediated disease associated problems is taught in Hanna, WO 90/15534, Dec. 27, 1990. In general, an initial treatment regimen can be copied from that known to be effective in interfering with TNF activity for other TNF mediated disease states by the compounds of Formula (I). Treated individuals will be regularly checked for T cell numbers and T4/T8 ratios and/or measures of viremia such as levels of reverse transcriptase or viral proteins, and/or for progression of monokine-mediated disease associated problems such as cachexia or muscle degeneration. If no effect is seen following the normal treatment regimen, then the amount of the monokine activity interfering agent administered is increased, e.g., by fifty percent per week.

The pharmaceutical composition of the present invention will comprise an effective, non-toxic amount of a compound of Formula (I) and a pharmaceutically acceptable carrier or diluent. The compounds of Formula (I) are administered in conventional dosage forms prepared by combining a compound of Formula (I) in an amount sufficient to produce TNF production inhibiting activity, respectively, with standard pharmaceutical carriers according to conventional procedures. These procedures may involve mixing, granulating, and compressing or dissolving the ingredients as appropriate to the desired preparation.

Thus, if a solid carrier is used, the preparation can be tableted, placed in a hard gelatin case in powder or pellet form, or in the form of a troche or lozenge. The amount of solid carrier will vary widely but preferably will be from about 25 mg to about 1 gram. When a liquid carrier is used, the preparation will be in the form of a syrup, emulsion, soft gelatin capsule, sterile injectable liquid such as an ampule or nonaqueous liquid suspension. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates, or oils and are incorporated in a soft gelatin capsule shell. A syrup formulation will generally consist of a suspension or solution of the compound or salt in a liquid carrier for example, ethanol, glycerine, or water with a flavoring or coloring agent.

The daily dosage regimen for oral administration is suitably about 0.001 mg/kg to 100 mg/kg, preferably 0.01 mg/Kg to 40 mg/Kg, of a compound of Formula (I) or a pharmaceutically acceptable salt thereof calculated as the free base. The active ingredient may be administered from 1 to 6 times a day, sufficient to exhibit activity.

While it is possible for an active ingredient to be administered neat, it is preferable to present it as a pharmaceutical formulation. The active ingredient may comprise, for topical administration, from 0.001% to 10% w/w, e.g., from 1% to 2% by weight of formulation, although it may comprise as much as 10% w/w but preferably not in excess of 5% w/w and more preferably from 0.1% to 1% w/w of Formulation.

Formulations of the present invention comprise an active ingredient together with one or more acceptable carrier(s) thereof and optionally any other therapeutic ingredient(s). The carrier(s) must be 'acceptable' in the sense of being compatible with the other ingredients of Formulation and not deleterious to the recipient thereof.

It will be recognized by one of skill in the art that the form and character of the pharmaceutically acceptable carrier or diluent is dictated by the amount of active ingredient with which it is to be combined, the route of administration, and other well-known variables.

No toxic effects are expected when these compounds are administered in accordance with the present invention.

Utility Examples

Example A

Inhibitory Effect of Compounds of Formula (I) on in vitro TNF Production by Human Monocytes The inhibitory effect of compounds of Formula (I) on in vitro TNF production by human monocytes may be determined by the protocol as described in Badger et al., EPO published Application 0 411 754 A2, Feb. 6, 1991, and in Hanna, WO 90/15534, Dec. 27, 1990.

Example B

Two models of endotoxic shock have been utilized to determine in vivo TNF activity for the compounds of Formula (I). The protocol used in these models is described in Badger et al., EPO published Application 0 411 754 A2, Feb. 6, 1991, and in Hanna, WO 90/15534, Dec. 27, 1990.

The exemplified compounds herein demonstrated a positive in vivo response in reducing serum levels of TNF induced by the injection of endotoxin.

Example C

Isolation of PDE Isozymes

The phosphodiesterase inhibitory activity and selectivity of the compounds of Formula (I) can be determined using a battery of five distinct PDE isozymes. The tissues used as sources of the different isozymes are as follows: 1) PDE Ib, porcine aorta; 2) PDE Ic, guinea-pig heart; 3) PDE III guinea-pig heart; 4) PDE IV, human monocyte; and 5) PDE V (also called "Ia"), canine tracheaolis. PDEs Ia, Ib, Ic and III are partially purified using standard chromatographic techniques [Torphy and Cieslinski, Mol. Pharmacol., 37:206–214, 1990]. PDE IV is purified to kinetic homogeneity by the sequential use of anion-exchange followed by heparin-Sepharose chromatography [Torphy et al., J. Biol. Chem., 267:1798–1804, 1992].

Phosphodiesterase activity is assayed as described in the protocol of Torphy and Cieslinski, Mol. Pharmacol., 37:206–214, 1990. Positive $IC_{50}$'s in the nanomolar to $\mu M$ range for compounds of the workings examples described herein for Formula (I) have been demonstrated.

Example D

The ability of selected PDE IV inhibitors to increase cAMP accumulation in intact tissues is assessed using U-937 cells, a human monocyte cell line that has been shown to contain a large amount of PDE IV. To assess the activity of PDE IV inhibition in intact cells, nondifferentiated U-937 cells (approximately $10^5$ cells/reaction tube) were incubated with various concentrations (0.01–1000 $\mu M$) of PDE inhibitors for one minute and 1 $\mu M$ prostaglandin E2 for an additional four minutes. Five minutes after initiating the reaction, cells were lysed by the addition of 17.5% perchloric acid, the pH was neutralized by the addition of 1M potassium carbonate and cAMP content was assessed by RIA. A general protocol for this assay is described in Brooker et al., Radioimmunassay of cyclic AMP and cyclic GMP., Adv. Cyclic Nucleotide Res., 10:1–33, 1979. The compounds of the working examples as described herein for Formula (I) have demonstrated a positive $EC_{50}$s in the $\mu M$ range in the above assay.

What is claimed is:

1. A compound of Formula (I):

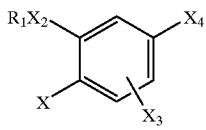

(I)

wherein:

$R_1$ is —$(CR_4R_5)_nC(O)O(CR_4R_5)_mR_6$, —$(CR_4R_5)_nC(O)NR_4(CR_4R_5)_mR_6$, —$(CR_4R_5)_nO(CR_4R_5)_mR_6$, or —$(CR_4R_5)_rR_6$ wherein the alkyl moieties may be optionally substituted with one or more halogens;

m is 0 to 2;

n is 1 to 4;

r is 0 to 6;

$R_4$ and $R_5$ are independently selected from hydrogen or a $C_{1-2}$ alkyl;

$R_6$ is hydrogen, methyl, hydroxyl, aryl, halo substituted aryl, aryloxy$C_{1-3}$ alkyl, halo substituted aryloxy$C_{1-3}$ alkyl, indanyl, indenyl, $C_{7-11}$ polycycloalkyl, tetrahydrofuranyl, furanyl, tetrahydropyranyl, pyranyl, tetrahydrothienyl, thienyl, tetrahydrothiopyranyl, thiopyranyl, $C_{3-6}$ cycloalkyl, or a $C_{4-6}$ cycloalkyl containing one or two unsaturated bonds, wherein the cycloalkyl and heterocyclic moieties may be optionally substituted by 1 to 3 methyl groups or one ethyl group;

provided that:
  a) when $R_6$ is hydroxyl, then m is 2; or
  b) when $R_6$ is hydroxyl, then r is 2 to 6; or
  c) when $R_6$ is 2-tetrahydropyranyl, 2-tetrahydrothiopyranyl, 2-tetrahydrofuranyl, or 2-tetrahydrothienyl, then m is 1 or 2; or
  d) when $R_6$ is 2-tetrahydropyranyl, 2-tetrahydrothiopyranyl, 2-tetrahydrofuranyl, or 2-tetrahydrothienyl, then r is 1 to 6;
  e) when n is 1 and m is 0, then $R_6$ is other than H in —$(CR_4R_5)_nO(CR_4R_5)_mR_6$;

X is $YR_2$, halogen, nitro, $NR_4R_5$, or formyl amine;

Y is O or $S(O)_{m'}$;

m' is 0, 1, or 2;

$X_2$ is O or $NR_8$;

$X_3$ is hydrogen or X;

$X_4$ is

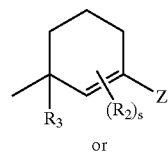

(a)

or

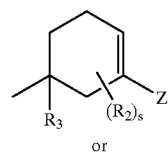

(b)

or

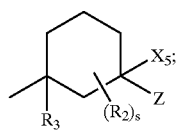

(c)

$X_5$ is H, $R_9$, $OR_8$, CN, $C(O)R_8$, $C(O)OR_8$, $C(O)NR_8R_8$, or $NR_8R_8$;

$R_2$ is independently —$CH_3$ or —$CH_2CH_3$ optionally substituted by 1 or more halogens;

s is 0 to 4;

$R_3$ is hydrogen, halogen, $C_{1-4}$ alkyl, $CH_2NHC(O)C(O)NH_2$, halo-substituted $C_{1-4}$ alkyl, —CH=$CR_8 R_{8'}$, cyclopropyl optionally substituted by $R_{8'}$, CN, $OR_8$, $CH_2OR_8$, $NR_8R_{10}$, $CH_2NR_8R_{10}$, C(Z')H, $C(O)OR_8$, $C(O)NR_8R_{10}$, or C≡$CR_{8'}$;

Z' is O, $NR_9$, $NOR_8$, NCN, C(—CN)$_2$, $CR_8$CN, $CR_8NO_2$, $CR_8C(O)OR_8$, $CR_8C(O)NR_8R_8$, C(—CN)$NO_2$, C(—CN)C(O)$OR_9$, or C(—CN)C(O)$NR_8R_8$;

Z is C(Y')$R_{14}$, C(O)$OR_{14}$, C(Y')$NR_{10}R_{14}$, C($NR_{10}$)$NR_{10}R_{14}$, CN, C(NOR$_8$)$R_{14}$, C(O)$NR_8NR_8C(O)R_8$, C(O)$NR_8NR_{10}R_{14}$, C(NOR$_{14}$)$R_8$, C($NR_8$)$NR_{10}R_{14}$, C($NR_{14}$)$NR_8R_8$, C(NCN)$NR_{10}R_{14}$, C(NCN)$SR_9$, (2-, 4- or 5-imidazolyl), (3-, 4- or 5-pyrazolyl), (4- or 5-triazolyl[1,2,3]), (3- or 5-triazolyl[1,2,4]), (5-tetrazolyl), (2-, 4- or 5-oxazolyl), (3-, 4- or 5-isoxazolyl), (3- or 5-oxadiazolyl[1,2,4]), (2-oxadiazolyl[1,3,4]), (2-thiadiazolyl[1,3,4]), (2-, 4- or 5-thiazolyl), (2-, 4-, or 5-oxazolidinyl), (2-, 4-, or 5-thiazolidinyl), or (2-, 4-, or 5-imidazolidinyl); wherein all of the heterocyclic ring systems may be optionally substituted one or more times by $R_{14}$;

Y' is O or S;

$R_7$ is —$(CR_4R_5)_qR_{12}$ or $C_{1-6}$ alkyl wherein the $R_{12}$ or $C_{1-6}$ alkyl group is optionally substituted one or more times by $C_{1-2}$ alkyl optionally substituted by one to three fluorines, —F, —Br, —Cl, —$NO_2$, —$NR_{10}R_{11}$, —$C(O)R_8$, —$C(O)OR_8$, —$OR_8$, —CN, —$C(O)NR_{10}R_{11}$, —$OC(O)NR_{10}R_{11}$, —$OC(O)R_8$, —$NR_{10}C(O)NR_{10}R_{11}$, —$NR_{10}C(O)R_{11}$, —$NR_{10}C(O)OR_9$, —$NR_{10}C(O)R_{13}$, —$C(NR_{10})NR_{10}R_{11}$, —C(NCN)$NR_{10}R_{11}$, —C(NCN)$SR_9$, —$NR_{10}C(NCN)SR_9$, —$NR_{10}C(NCN)NR_{10}R_{11}$, —$NR_{10}S(O)_2R_9$, —$S(O)_{m'}R_9$, —$NR_{10}C(O)C(O)NR_{10}R_{11}$, —$NR_{10}C(O)C(O)R_{10}$, thiazolyl, imidazolyl, oxazolyl, pyrazolyl, triazolyl, or tetrazolyl;

q is 0, 1, or 2;

$R_{12}$ is $C_{3-7}$ cycloalkyl, (2-, 3- or 4-pyridyl), pyrimidyl, pyrazolyl, (1- or 2-imidazolyl), thiazolyl, triazolyl, pyrrolyl, piperazinyl, piperidinyl, morpholinyl, furanyl, (2- or 3-thienyl), (4- or 5-thiazolyl), quinolinyl, naphthyl, or phenyl;

$R_8$ is hydrogen or $R_9$;

$R_{8'}$ is $R_8$ or fluorine;

$R_9$ is $C_{1-4}$ alkyl optionally substituted by one to three fluorines;

$R_{10}$ is $OR_8$ or $R_{11}$;

$R_{11}$ is hydrogen, or $C_{1-4}$ alkyl optionally substituted by one to three fluorines; or when $R_{10}$ and $R_{11}$ are as $NR_{10}R_{11}$ they may together with the nitrogen form a 5 to 7 membered ring optionally containing at least one additional heteroatom which is O, N, or S;

$R_{13}$ is oxazolidinyl, oxazolyl, thiazolyl, pyrazolyl, triazolyl, tetrazolyl, imidazolyl, imidazolidinyl, thiazolidinyl, isoxazolyl, oxadiazolyl, or thiadiazolyl, and each of these heterocyclic rings is connected through a carbon atom and each may be unsubstituted or substituted by one or two $C_{1-2}$ alkyl groups;

$R_{14}$ is hydrogen or $R_7$; or when $R_{10}$ and $R_{14}$ are as $NR_{10}R_{14}$ they may together with the nitrogen form a 5 to 7 membered ring optionally containing at least one additional heteroatom which is O, N, or S;

provided that:

f) when $R_{12}$ is N-pyrazolyl, N-imidazolyl, N-triazolyl, N-pyrrolyl, N-piperazinyl, N-piperidinyl, or N-morpholinyl, then q is not 1; or or the pharmaceutically acceptable salts thereof.

2. A pharmaceutical composition comprising a compound of Formula (I) according to claim 1 and a pharmaceutically acceptable excipient.

3. A method for treating an allergic or inflammatory state which method comprises administering to a subject in need thereof an effective amount of a compound of Formula (I) according to claim 1 alone or in combination with a pharmaceutically acceptable excipient.

4. A compound of claim 1 which is:

methyl 5-cyano-5-(3-cyclopropylmethoxy-4-methoxyphenyl)cyclohex-1-ene-1-carboxylate;

ethyl 5-cyano-5-(3-cyclopropylmethoxy-4-methoxyphenyl)cyclohex-1-ene-1-carboxylate;

methyl 5-cyano-5-(3-cyclopentyloxy-4-methoxyphenyl)cyclohex-1-ene-1-carboxylate;

methyl 5-cyano-5-(3,4-bisdifluoromethoxyphenyl)cyclohex-1-ene-1-carboxylate;

methyl cis-[3-cyano-3-(3-cyclopropylmethoxy-4-methoxyphenyl)-cyclohexane-1-carboxylate];

ethyl cis-[3-cyano-3-(3-cyclopropylmethoxy-4-methoxyphenyl)-cyclohexane-1-carboxylate];

methyl cis-[3-cyano-3-(3-cyclopentyloxy-4-methoxyphenyl)cyclohexane-1-carboxylate];

methyl cis-[3-(3,4-bisdifluoromethoxyphenyl)-3-cyanocyclohexane-1-carboxylate];

cis-[3-cyano-3-(3-cyclopropylmethoxy-4-methoxyphenyl)cyclohexane-1-carboxylic acid]; cis-[3-cyano-3-(3-cyclopentyloxy-4-methoxyphenyl)cyclohexane-1-carboxylic acid];

cis-[3-cyano-3-(3-cyclopropylmethoxy-4-methoxyphenyl)cyclohexane-1-carboxamide]; cis-[3-cyano-3-(3-cyclopropylmethoxy-4-methoxyphenyl)cyclohexane-1-N-methylcarboxamide]; cis-[3-cyano-3-(3-cyclopropylmethoxy-4-methoxyphenyl)cyclohexane-1-N,N-dimethylcarboxamide]; cis-[3-cyano-3-(3-cyclopropylmethoxy-4-methoxyphenyl)cyclohexane-1-{N-(4-bromobenzyl)carboxamide}];

cis-[3-cyano-3-(3-cyclopentyloxy-4-methoxyphenyl)cyclohexane-1-carboxamide];

cis-[3-(3-cyclopropylmethoxy-4-methoxyphenyl)-1,3-dicyano-cyclohexane];

cis-[3-(3-cyclopentyloxy-4-methoxyphenyl)-1,3-dicyanocyclohexane]; cis-{3-cyano-3-(3-cyclopropylmethoxy-4-methoxyphenyl)-1-(3-methyl[1,2,4]oxadiazol-5-yl)cyclohexane}; cis-{3-cyano-3-(3-cyclopentyloxy-4-methoxyphenyl)-1-(3-methyl[1,2,4]-oxadiazol-5-yl)cyclohexane}; trans-[3-cyano-3-(3-cyclopropylmethoxy-4-methoxyphenyl)-cyclohexane-1-carboxylate];

trans-[3-cyano-3-(3-cyclopentyloxy-4-methoxyphenyl)-cyclohexane-1-carboxylate]; trans-[3-cyano-3-(3-cyclopropylmethoxy-4-methoxyphenyl)cyclohexane-1-carboxylic acid];

trans-[3-cyano-3-(3-cyclopentyloxy-4-methoxyphenyl)cyclohexane-1-carboxylic acid];

trans-[3-cyano-3-(3-cyclopropylmethoxy-4-methoxyphenyl)cyclohexane-1-carboxamide]; trans-[3-cyano-3-(3-cyclopentyloxy-4-methoxyphenyl)cyclohexane-1-carboxamide]; trans-[3-(3-cyclopropylmethoxy-4-methoxyphenyl)-1,3-dicyanocyclohexane]; trans-[3-(3-cyclopentyloxy-4-methoxyphenyl)-1,3-dicyanocyclohexane];

trans-{3-cyano-3-(3-cyclopentyloxyphenyl)-1-(3-methyl[1,2,4]oxadiazol-5-yl)cyclo-hexane};

3-cyano-3-(3-cyclopentyloxy-4-methoxyphenyl)cyclohex-1-ene-1-carboxylate;

5-cyano-5-(3-cyclopentyloxy-4-methoxyphenyl)cyclohex-1-ene-1-carboxylate;

3-(3-cyclopentyloxy-4-methoxyphenyl)cyclohex-1-ene-1,3-dicarbonitrile; or 5-(3-cyclopentyloxy-4-methoxyphenyl)cyclohex-1-ene-1,5-dicarbonitrile.

\* \* \* \* \*